United States Patent [19]
Dubois et al.

[11] Patent Number: 5,859,340
[45] Date of Patent: Jan. 12, 1999

[54] RECOMBINANT GENE CODING FOR A PROTEIN HAVING ENDOCHITINASE ACTIVITY

[75] Inventors: Michel Dubois, Buc; René Grison, Escalquens; Jean-Jacques Leguay, Auzeville Tolosane; Annie Pignard, Roquettes; Alain Toppan, Cornebarrieu, all of France

[73] Assignees: Sanofi, Paris; Elf Aquitaine, Courbevoie, both of France

[21] Appl. No.: 475,427

[22] Filed: Jun. 7, 1995

Related U.S. Application Data

[63] Continuation of Ser. No. 842,165, May 1, 1992, which is a continuation of PCT/FR91/00607 Jul. 24, 1991.

[30] Foreign Application Priority Data

Jul. 24, 1990 [FR] France .................. 90 09460

[51] Int. Cl.$^6$ .............. A01H 5/00; C12N 15/29; C12N 15/56; C12N 15/62; C12N 15/82
[52] U.S. Cl. .............. 800/205; 800/250; 800/DIG. 14; 800/DIG. 17; 800/DIG. 43; 536/23.2; 536/23.4; 536/23.6; 536/24.1; 435/69.1; 435/69.7; 435/69.8; 435/70.1; 435/172.3; 435/200; 435/414; 435/416; 435/418; 435/419
[58] Field of Search .................. 536/23.6, 23.2, 536/23.4, 24.1; 435/69.1, 70.1, 172.3, 69.7, 69.8, 200, 240.4, 418, 419, 414, 416; 800/205, 250, DIG. 14, DIG. 17, DIG. 43

[56] References Cited

FOREIGN PATENT DOCUMENTS 292 435  11/1988  European Pat. Off. .
WO 90/07001  6/1990  WIPO .

OTHER PUBLICATIONS

Shishi et al, Plant Molecular Biology, vol. 14, 1990, pp. 357–368.
Durand–Tardif, Pascal Abrege No. 88–0108006.
Linthorst et al, Molecular Plant–Microbe Interactions, vol. 3, No. 4, pp. 252–258.
Gaynor, Nucleic Acids Research, 16(11):5210 (1988).
Laflamme et al, Plant Molecular Biology, 13:249–250 (1989).
Gaynor et al, Nucleic Acids Research, 17(14):5855–5856, (1989).
Hedrick et al, Plant Physiol, 86:182–186 (1988).
Graham et al. 1994, DTF Can. J. Bot. 72, 1057–1083.
Lewin, R. 1987, Science 237:1570.
Reeck et al. 1987. Cell 50:667.
Bennetzen et al. 1992. pp. 99–124 In: Genetic Engineering, vol. 14, J. Setlow, ed., Plenum Press: New York.

*Primary Examiner*—David T. Fox
*Attorney, Agent, or Firm*—Foley & Lardner

[57] ABSTRACT

Recombinant gene coding for a protein having endochitinase activity or for a precursor thereof which comprises the sequence of SEQ ID NO:1 below:

Gly Gly Asp Leu Gly Ser VaL Ile Ser Asn Ser Met Phe Asp Gln Met Leu Lys His Arg Asn Glu Asn Ser Cys Gln Gly Lys Asn Asn Phe Tyr Ser Tyr Asn Ala Phe Ile Thr Ala Ala Arg Ser Phe Pro Gly, Phe Gly Thr Ser Gly Asp Ile Asn Ala Arg Lys Arg Glu Ile Ala Ala Phe Phe Ala Gln Thr Ser His Glu Thr Thr Gly Gly Trp Pro Ser Ala Pro Asp Gly Pro Phe Ala Trp Gly Tyr Cys Phe Leu Arg Gly Arg Gly Asn Pro Gly Asp Tyr Cys Ser Pro Ser Ser Gln Trp Pro Cys Ala Pro Gly Arg Lys Tyr Phe Gly Arg Gly Pro Ile Gln Ile Ser His Asn Tyr Asn Tyr Gly Pro Cys Gly Arg Ala Ile Gly Val Asp Leu Leu Asn Asn Pro Asp Leu Val Ala Thr Asp Pro Val Ile Ser Phe Lys Thr Ala Ile Trp Phe Trp Met Thr Pro Gln Ser Pro Lys Pro Ser Cys His Asp Val Ile Ile Gly Arg Trp Asn Pro Ser Ala Gly Asp Arg Ser Ala Asn Arg Leu Pro Gly Phe Gly Val Ile Thr Asn Ile Ile Asn Gly Gly Leu Glu Cys Gly Arg Gly Asn Asp Asn Arg Val Gln Asp Arg Ile Gly Phe Tyr Arg Arg Tyr Cys Gly Ile Leu Gly Val Ser Pro Gly Asp Asn Leu Asp Cys Gly Asn Gln Arg Ser Phe Gly Asn Gly Leu Leu Val Asp Thr Met.

Application: For obtaining plants resisting to pathogenic agents.

18 Claims, 17 Drawing Sheets

FIG. 2A

EcoRI
GAATTCATATATTTATTTAAAAAAATATTTCAACTTCAAAAAATATATTTTTTCACGCCT
ACCCTCGACCCCCTCCCGCACCCTTACCCGCCCTCTACCAACCCCCCCCCCCAAAAA
AAAATAAATTAAAGTTTACTTTTAAAAATATTTCAACTTCAAAATTTCATTTTTTTCA
TCCCTACCCTCGACCACCCCACCCTCCCGCTAAAAATAAAGTTTAAGTTTGTTTTTG
AAAAGTATTTTCAACTTCAAAATTCATTTTTCACCCTAACCTCAACCCCCACCCAC
ATTCCCACCCCAATTTTTTTTTTAAGTTGTTGTTAAAAATATTTTCTACTTCAAAAT
TTCATTTCACCCTTTCCCCCCCTCCCCCCAACCCCACCCTTAATTTCAATTTTCTATTC
AAAAATATTTAAATTGTTTTAAAAATATCTCAAAACATTTTTTACTTATTCAAAAACCAAACACTC
TAGTAAAATAAAGATATATCTCAAAACATTTTTTACTTATTCAAAATAAATCAAAATCTAGTT
TTTTCCAGAAAAATTTCTATTCACCAACCAAATATGAGAAAATAAATCAAAATCTAGTT

FIG. 2B

ATTTTAGAAAATGTTTCCTACATATCAAACACACCCAATGTCTTCATTAATGTGTTCAG
ATTTATTTTATGTCAACTTGGTCGCTATGTTATATGAATTAGCCACACAAATTCAATTTA
ATTGCACATTACCACTATTTTGTAGTTCACGTAGAAATTAAAGTTCATCACAACAAAATA
AATATTGGGCGCACGGGCGACTCCCCACTAGTATCACTCAGAAATCACAATAAAGTATTA
AATTTGTCAAAATTCTTTATCCGTATTAAGAAATCTTTGAAGTCTGAATACATATAAAT
TCATAATTCATAAATTTCAAATTTCTCTTAGTAATTTTATTGAGTTATTAATTTCATTT
AAACAAATTCATTGTACTTTGTAAATACTCCTAATTTGTATGATTTTGGACTCATGTAAG
GAAACCCTTATCAAATTAAGTATGGAGTTAAAGGGAAGAGTAGAATTAGCAGCCCAAAGA
TACACTTTCAAATTATGTAAGTTTGACCCAGCCTGCCCTATTTCTTCTAGCACCAGCTGC
TACCTTTATATAATTACTTTAATTTGAAAATGTCATCAATATCATGCAAAATTTACCGGCC
CTATTTCTTCTAGCACTAGCTACTACCTTATATAATTACTTTAATTTGTAAGTGTCATCA

FIG. 2C

ATATCATGCAAAATTTAGTCAAAATATTTATCTCGATGTCTTTGGTTCTCAAATAGAGCA
AATAGACTCAGACTCGAACCTACGCAAGTGTAAAAGCAAGGAATGATTACCAAACAAGAC
AGTTCTCAACAAGCAACAAAATAAACAAGGCAAAACTAGTTAGAAAACGAATGCTATTGT
CATTCCAGCCGAACTAACAATAACCTACATACAAACCAGTTCAACCTTTAGCTTTACTTT
TACCATTTTTGGCTCTTTTGTTAATTGAGATTTGAAATAAATCTCAACAATAATTTATTT
ATGATCCACATGACATTAGTCTAAGAGGTGATTGAACATTACTTGAGAGATATTGCTATT
CGATGAGTTACATAGTTTTCCACTACAAATTTAATTTACTCTAACTATGAATATTATAAT
TTGTAGTACAGTTTTTATTTAATAGGTAAATTTAATAAGAGTAAACAAAAAATATCCAGC
AACTATAGTCTCCAGTCCAAATTATGTAGAGAAAAGTCTGGAATAACGTCCAAAGCCGCC
CGTCTCTTTTACTTATAACTGAATTAAATTCTGGATACGACAGGGTGGACTATCAATTTT
GTCATAAAAGTCACTGATTCCTCACAACCACTTGCCTATAAATAGCTTTCACTTTAGCAT

FIG. 2D

TTGTTTGCCATCACATTCAAAATGAGGCGAACTTCTAAATTGACTACTTTTCTTTGCTG
                   MetArgArgThrSerLysLeuThrThrPheSerLeuLeu
                   StyI 2006
                   ↓
TTTTCTCTGGTTTTGCTGAGTGCTGCCTTGGCACAGAATTGTGGTTCACAGGGCGGAGGC
PheSerLeuValLeuLeuSerAlaAlaLeuAlaGlnAsnCysGlySerGlnGlyGlyGly

AAAGTTTGTGCGTCGGGACAATGTTGCAGCAAATTCGGGTGGTGCGGTAACACTAATGAC
LysValCysAlaSerGlyGlnCysCysSerLysPheGlyTrpCysGlyAsnThrAsnAsp

CATTGTGGTTCTGGCAATTGTCAAAGTCAGTGTCCAGGTGGCGGCCCTGGTCCTGGTCCT
HisCysGlySerGlyAsnCysGlnSerGlnCysProGlyGlyGlyProGlyProGlyPro
         PraII (1)
         ↓
GTTACTGGTGGGGACCTCGGAAGCGTCATCTCAAATTCTATGTTTGATCAAATGCTTAAG
ValThrGlyGlyAspLeuGlySerValIleSerAsnSerMetPheAspGlnMetLeuLys

CATCGTAACGAAAATTCTTGTCAAGGAAAGAATAATTCTACAGTTACAATGCCTTTATT
HisArgAsnGluAsnSerCysGlnGlyLysAsnAsnPheTyrSerTyrAsnAlaPheIle

FIG. 2E

ACTGCTGCTAGGTCTCTTTTCCTGGCTTTGGTACAAGTGGTGATATCAATGCCCGTAAAAGG
ThrAlaAlaArgSerPheProGlyPheGlyThrSerGlyAspIleAsnAlaArgLysArg

GAAATTGCTGCTTTCTTTGCCCAAACCCTCCCATGAAACTACTGGTATGTGTATAACCATT
GluIleAlaAlaPhePheAlaGlnThrSerHisGluThrThrG

CACATCGAACCATTAAAATATAATTTCATTTTATTTTAGTAATTGATTATATATGT

AGGAGGATGGCCTTCCGCCACCTGATGGACCATTCGCATGGGGTTACTGTTTCCTTAGAGA
lyGlyTrpProSerAlaProAspGlyProPheAlaTrpGlyTyrCysPheLeuArgGl

ACGAGGTAACCCCGGTGACTACTGTTCACCAAGTAGTCAATGGCCTTGTGCACCTGGAAG
uArgGlyAsnProGlyAspTyrCysSerProSerSerGlnTrpProCysAlaProGlyAr

GAAATATTTCGGACGAGGCCCAATCCAAATTTCACAGTAAGCTACATAAATCTATATATG
gLysTyrPheGlyArgGlyProIleGlnIleSerHi

FIG. 2F

```
GTAAAATTTGATGAACTTGTAGTGTCTAATTACGTGTATTTGACATTTCAAAACAGCAA
                                                   sAs

CTACAACTATGGCCATGTGGAAGAGCCATCGGAGTGGACCTTTAAACAATCCTGATTT
nTyrAsnTyrGlyProCysGlyArgAlaIleGlyValAspLeuLeuAsnAsnProAspLe

AGTAGCCACAGACCCAGTCATCTCATTCAAGACTGCTATCTGGTTCTGGATGACCCCTCA
uValAlaThrAspProValIleSerPheLysThrAlaIleTrpPheTrpMetThrProGl

ATCACCAAAGCCTTCTTGCCACGATGTCATCATTGGAAGATGGAACCCATCTGCCGGTGA
nSerProLysProSerCysHisAspValIleIleGlyArgTrpAsnProSerAlaGlyAs
                                                  DraII (2)

CCGATCAGCCAATCGTCTTCCTGGATTTGGTGTCATCACAAACATCATCAATGGGGCCT
pArgSerAlaAsnArgLeuProGlyPheGlyValIleThrAsnIleIleAsnGlyGlyLe

AGAAATGTGGTCGTGGTAATGACAACAGGGTACAAGATCGAATTGGATTTTACAGGAGTA
uGluCysGlyArgGlyAsnAspAsnArgValGlnAspArgIleGlyPheTyrArgArgTy
          HindIII 3007

TTGCGGAAGCTT
rCysGly
```

FIG. 3A

```
                                                                           .                    5
  1     .........................................................TCTCT
                                                                           .                   50
  1     ATGAGGCGAACTTCTAAATTGACTACTTTTTCTTTGCTGTGTTTTCTCTGGT
                                                                           .                   55
  6     CCTACTCCTCTCTGCCTCGGCAGAGAACAATGTGGTTCGCAGGCGGGAGGTG
                ||||  ||||| ||||||| ||   ||||| ||||||| ||||| |||||| |
                                                                           .                  100
 51     TTTGCTGAGTGCTGCCTTGGCACAGAATTGTGGTTCACAGGGCGGAGGCA
                                                                           .                  105
 56     CGCGTTGTGCCTCGGGTCTCTGCTGCAGCAAATTTGGTTGGTGTGGTAAC
                 ||||  |||| |||||| ||||||||||||  |||| |||| ||||||
                                                                           .                  150
101     AAGTTTGTGCGTCGGGACAATGTTGCAGCAAATTCGGGTGGTGCGGTAAC
                                                                           .                  155
106     ACCAATGACTATTGTGGCCCTGGCAATTGCCAGAGAGCCAGTGCCCTGGTG
                ||||||| || |||||| |||||||||||  ||||||||||| |||||||
                                                                           .                  200
151     ACTAATGACCATTGTGGTTCTGGCAATTGTCAAAGTGTCAGTGTCCAGGTGG
                                                                           .                  196
156     TCCCACACCACCCGG..........TGGTGGGGATCTCGGCAGTATCATCT
                                                                           .                  250
201     CGGCCCTGGTCCTGTCCTGTTACTGGTGGGGACCTCGGAAGCGTCATCT
```

FIG. 3B

```
197  CAAGTTCCATGTTTGATCAGATGCTTAAGCATCGCAACGATAATGC  246
     |||||| ||||||||||||| |||||||||||| |||| |||||||
251  CAAATTCTATGTTTGATCAAATGCTTAAGCATCGTAACGAAAATTCTTGT  300

247  CAAGGAAAG...GGATTCTACAGTTACAATGCCTTTATCAATGCTGCTAG  293
     ||||||||    ||||||||||||||||||||||||| |||||||||||
301  CAAGGAAAGAATAATTTCTACAGTTACAATGCCTTTATTACTGCTGCTAG  350

294  GTCTTTTCCTGGCTTTGGTACTAGTGGTGATACCACTGCCCGTAAAAGAG  343
     |||||||||||||||||||||||| ||||| ||| ||||||||||| ||
351  GTCTTTTCCTGGCTTTGGTACAAGTGGTGATATCAATGCCCGTAAAAGGG  400

344  AAATCGCGGGCTTTCTTCGCCCAAACCTCCCATGAAACTACAGGAGGATGG  393
     |||| ||||||||||||||| ||||||||||||||||||||| |||||||
401  AAATTGCTGCTTTCTTTGCCCAAACCTCCCATGAAACTACTGGAGGATGG  450

394  GCAACAGCACCAGATGGTCCATACGCCGTGGGGTTACTGCTGCTTAGAGA  443
      |      ||||||| ||   ||||  | |||||||||| |||||||||
451  CCTTCCGCACCTGATGGACCATTCGCATGGGGTTACTGTTTCCTTAGAGA  500
```

FIG. 3C

```
444  ACAAGGTAGCCCCGGCGACTACTGTACACCAAGTGGTCAGTGGCCTTGTG  493
     ||  ||||| |||||| |||||||||||||||||||| |||||||||||||
501  ACGAGGTAACCCCGGTGACTACTGTTCACCAAGTAGTCAATGGCCTTGTG  550

494  CTCCTGGTCGGAAAATATTTCGGACGAGGCCCCATCCAAATTTCACACAAC  543
     |||||| |  ||| ||||||||||||||||||||||||||||||||||||
551  CACCTGGAAGGAAATATTTCGGACGAGGCCCAATCCAAATTTCACACAAC  600

544  TACAACTACGGACCCTTGTGGAAGAGCCATAGGAGTGGACCTCCTAAACAA  593
     |||||||| |||  ||||||||||||||||  ||||||||||||| ||||||
601  TACAACTATGGGCCATGTGGAAGAGCCATCGGAGTGGACCTTTTAAACAA  650

594  TCCTGATTTAGTGGCCACAGATCCAGTAATCTCATTCAAGTCAGCTCTCT  643
     ||||||||||||| ||||||| ||||| ||||||||||||||||| ||||
651  TCCTGATTTAGTAGCCACAGACCCAGTCATCTCATTCAAGACTGCTATCT  700

644  GGTTTTGGATGACTCCTCAATCACCAAAACCTTCTTGCCACGATGTCATC  693
     ||||| ||||||||||||||||||||||| ||||||||||||||||||||
701  GGTTCTGGATGACCCCTCAATCACCAAAGCCTTCTTGCCACGATGTCATC  750
```

FIG. 3D

```
694  ATTGGAAGATGGCAACCATCGTCTGCTGACCGCGCAGCCAATCGTCTCCC  743
     ||||||||||||||||||| ||||||||| ||||| |||||||||||||||
751  ATTGGAAGATGGAACCCATCTGCCGGTGACCGATCAGCCAATCGTCTTCC  800

744  TGGATTTGGTGTCATCACGAACATCATCAATGGTGGCTTGGAATGTGGTC  793
     |||||||||||||||||||| ||||||||||||  ||||||||||||||||
801  TGGATTTGGTGTCATCACAAACATCATCAATGGGGGCCTGGAATGTGGTC  850

794  GTGGCACTGACTCAAGGGTCCAGGATCGGCATTGGGTTTTACAGGAGGTAT  843
     |||||| ||||  |||||||||||||| |||||||||||||||||||||||
851  GTGGCAATGACAATAGGGTCCAGGATCGCCATTGGGTTTTACAGGAGGTAT  900

844  TGCAGTATTCTTGGTGTGTTAGTCCTGGTGACAATCTTGATTGCGGAAACCA  893
     ||| |
901  TGCGG

894  GAGGTCTTTTGGAAACGGACTTTTAGTCGATACTATGTAATTTTATGGTC  943
```

FIG. 4A

BamHI
→
GGATCCATGAGGCGGAACTTCTAAATTGACTACTTTTTCTTTGCTGTGTTTTCTCTGGTTTG
　　　MetArgArgThrSerLysLeuThrThrPheSerLeuLeuPheSerLeuValLeu
　　　　　　　　　　　　　　　　→
　　　　　　　　　sequence (3)

CTGAGTGCTGCCCTTGGCACAGAATTGTGGTTCACAGGGCGGAGGCAAAGTTTGTGCGTCG
LeuSerAlaAlaLeuAlaGlnAsnCysGlySerGlnGlyGlyGlyLysValCysAlaSer
　　　　　　　　　　　　　　　←
　　　　　　　　　　sequence (2)

GGACAATGTTGCAGCAAATTCGGGTGGTGCGGTAACACTAATGACCATTGTGGTTCTGGC
GlyGlnCysCysSerLysPheGlyTrpCysProValThrAsnAspHisCysGlySerGly

AATTGTCAAAGTCAGTGTCCAGGTGGCGGGCCCCTGGTCCCTGTTACTGGTGGGGAC
AsnCysGlnSerGlnCysProGlyGlyGlyProGlyProValThrGlyGlyAsp
　　　　　　　　　　　　　　　　　　　　　　　　　　　　　→

CTCGGAAGCGTCATCTCAAATTCTATGTTTGATCAAATGCTTAAGCATCGTAACGAAAAT
LeuGlySerValIleSerAsnSerMetPheAspGlnMetLeuLysHisArgAsnGluAsn

TCTTGTCAAGGAAAGAATAATTTCTACAGTTACAATGCCTTTATTACTGCTGCTAGGTCT
SerCysGlnGlyLysAsnAsnPheTyrSerTyrAsnAlaPheIleThrAlaAlaArgSer

TTTCCTGGCTTTGGTACAAGTGGTGATATCAATGCCCGTAAAAGGGAAATTGCTGCTTTC
PheProGlyPheGlyThrSerGlyAspIleAsnAlaArgLysArgGluIleAlaAlaPhe

FIG. 4B

TTTGCCAAACCTCCCATGAAACTACTGGTATGTGTATAACCATTCACATGAACCATTA
PheAlaGlnThrSerHisGluThrThrG

AAATATAATTTCATTTTATTTTAGTAATTGATTATATATATGTAGGAGGATGGCCTTC
lyGlyTrpProSe

CGCACCTGATGGACCATTCGCATGGGGTTACTGTTTCCTTAGAGAACGAGGTAACCCCGG
rAlaProAspGlyProPheAlaTrpGlyTyrCysPheLeuArgGluArgGlyAsnProGl

TGACTACTGTTCACCAAGTAGTCAATGGCCTTGTGCACCTGGAAGGAAATATTTCGGACG
yAspTyrCysSerProSerSerGlnTrpProCysAlaProGlyArgLysTyrPheGlyAr

AGGCCCAATCCAAATTTCACAGTAAGCTACATAAATCTATATATGGTAAAATTTGATGAA
gGlyProIleGlnIleSerHi

CTTGTGTAGTGTCTAATTACGTGTATTTGACATTTCAAAACAGCAACTACAACTATGGCC
sAsnTyrAsnTyrGlyPr

ATGTGGAAGAGCCATCGGAGTGGACCTTTTAAACAATCCTGATTTAGTAGCCACAGACCC
oCysGlyArgAlaIleGlyValAspLeuLeuAsnAsnProAspLeuValAlaThrAspPr

FIG. 4C

AGTCATCTCATTCAAGACTGCTATCTGGTTCTGGATGACCCCTCAATCACCAAAGCCTTC
oValIleSerPheLysThrAlaIleTrpPheTrpMetThrProGlnSerProLysProSe

TTGCCACGATGTCATCATTGGAAGATGGAACCCATCTGCCGGTGACCGATCAGCCAATCG
rCysHisAspValIleIleGlyArgTrpAsnProSerAlaGlyAspArgSerAlaAsnAr

TCTTCCTGGATTGGTGTCATCACAAACATCATCAATGGGGCCTGGAATGTGGTCGTGG
gLeuProGlyPheGlyValIleThrAsnIleIleAsnGlyGlyLeuGluCysGlyArgGl

CAATGACAATAGGGTCCAGGATCGCATTGGGTTTTACAGGAGGTATTGCGGTATTCTTGG
yAsnAspAsnArgValGlnAspArgIleGlyPheTyrArgArgTyrCysGlyIleLeuGl

TGTTAGTCCTGGTGACAATCTTGATTGCGGAAACCAGAGATCTTTTGGAAACGGACTTTT
yValSerProGlyAspAsnLeuAspCysGlyAsnGlnArgSerPheGlyAsnGlyLeuLe

AGTCGATACTATGTAATGAGCTC
uValAspThrMetEndEnd   ↑
                     SacI

FIG. 5A

```
AAGCTTGCAC GACACACTTG TCTACTCCAA AAATATCAAA GATACAGTCC
TCAGAAGACC AAAGGGCCAA TTGAGACTTT TCAACAAAGG GTAATATCCG
GAAACCTCCT CGGATTCCAT TGCCCAGCTA TCTGTCACTT TATTGTGAAG
ATAGTGGAAA AGGAAGGTGG CTCCTACAAA TGCCATCATT GCGATAAAGG
AAAGGCCATC GTTGAAGATG CCTCTGCCGA CAGTGGTCCC AAAGATGGAC
CCCCACCCAC GAGGAGCATC GTGGAAAAAG AAGACGTTCC AACCACGTCT
TCAAAGCAAG TGGATTGATG TGATATCTCC ACTGACGTAA GGGATGACGC
ACAATCCCAC TATCCTTCGC AAGACCCTTC CTCTATATAA GGAAGTTCAT
TTCATTTGGA GAGAACACGG GGGACTCTAG AGGATCCATG AGGCGAACTT
CTAAATTGAC TACTTTTTCT TTGCTGTTTT CTCTGGTTTT GCTGAGTGCT
GCCTTGGCAC AGAATTGTGG TTCACAGGGC GGAGGCAAAG TTTGTGCGTC
GGGACAATGT TGCAGCAAAT TCGGGTGGTG CGGTAACACT AATGACCATT
GTGGTTCTGG CAATTGTCAA AGTCAGTGTC CAGGTGGCGG CCCTGGTCCT
GGTCCTGTTA CTGGTGGGGA CCTCGGAAGC GTCATCTCAA ATTCTATGTT
TGATCAAATG CTTAAGCATC GTAACGAAAA TTCTTGTCAA GGAAAGAATA
ATTTCTACAG TTACAATGCC TTTATTACTG CTGCTAGGTC TTTTCCTGGC
TTTGGTACAA GTGGTGATAT CAATGCCCGT AAAAGGGAAA TTGCTGCTTT
```

FIG. 5B

```
CTTTGCCCAA ACCTCCCATG AAACTACTGG TATGTGTATA ACCATTCACA
TCGAACCATT AAAATATAAT TTCATTTTAT TTTATTTAGT AATTGATTAT
ATATGTAGGA GGATGGCCTT CCGCACCTGA TGGACCATTC GCATGGGGTT
ACTGTTTCCT TAGAGAACGA GGTAACCCCG GTGACTACTG TTCACCAAGT
AGTCAATGGC CTTGTGCACC TGGAAGGAAA TATTTCGGAC GAGGCCCAAT
CCAAATTTCA CAGTAAGCTA CATAAATCTA TATATGGTAA AATTTGATGA
ACTTGTAGTG TCTAATTACG TGTATTTTGA CATTTCAAAA CAGCAACTAC
AACTATGGGC CATGTGGAAG AGCCATCGGA GTGGACCTTT TAAACAATCC
TGATTTAGTA GCCACAGACC CAGTCATCTC ATTCAAGACT GCTATCTGGT
TCTGGATGAC CCCTCAATCA CCAAAGCCTT CTTGCCACGA TGTCATCATT
GGAAGATGGA ACCCATCTGC CGGTGACCGA TCAGCCAATC GTCTTCCTGG
ATTTGGTGTC ATCACAAACA TCATCAATGG GGGCCTGGAA TGTGGTCGTG
GCAATGACAA TAGGGTCCAG GATCGCATTG GGTTTTACAG GAGGTATTGC
GGTATTCTTG GTGTTAGTCC TGGTGACAAT CTTGATTGCG GAAACCAGAG
ATCTTTTGGA AACGGACTTT TAGTCGATAC TATGTAATGA GCTCGAATTT
CCCCGATCGT TCAAACATTT GGCAATAAAG TTTCTTAAGA TTGAATCCTG
TTGCCGGTCT TGCGATGATT ATCATATAAT TTCTGTTGAA TTACGTTAAG
CATGTAATAA TTAACATGTA ATGCATGACG TTATTTATGA GATGGGTTTT
TATGATTAGA GTCCGCAAT TATACATTTA ATACGCGATA GAAAACAAAA
TATAGCGCGC AAACTAGGAT AAATTATCGC GCGCGGTGTC ATCTATGTTA
CTAGATCGAA TTC
```

FIG. 6

SerValIleSerAsnSerMetPheAspGlnMetLeuLysHisArgAsnGluAsnSerCys
GlnGlyLysAsnAsnPheTyrSerTyrAsnAlaPheIleThrAlaAlaArgSerPhePro
GlyPheGlyThrSerGlyAspIleAsnAlaArgLysArgGluIleAlaAlaPhePheAla
GlnThrSerHisGluThrThrGlyGlyTrpGlyProSerAlaProAspGlyProPheAlaTrp
GlyTyrCysPheLeuArgGluArgGlyAsnProGlyAspTyrCysSerProSerSerGln
TrpProCysAlaProGlyArgGlyTyrPheGlyArgGlyProIleGlnIleSerHisAsn
TyrAsnTyrGlyProCysGlyArgAlaIleGlyValAspLeuLeuAsnAsnProAspLeu
ValAlaThrAspProValIleSerPheLysThrAlaIleTrpPheTrpMetThrProGln
SerProLysProSerCysHisAspValIleIleGlyArgTrpAsnProSerAlaGlyAsp
ArgSerAlaAsnArgLeuProGlyPheGlyValIleThrAsnIleIleAsnGlyGlyLeu
GluCysGlyArgGlyAsnAspAsnArgValGlnAspArgIleGlyPheTyrArgArgTyr
CysGlyIleLeuGlyValSerProGlyAspAsnLeuAspCysGlyAsnGlnArgSerPhe
GlyAsnGlyLeuLeuValAspThrMet
GlyGlyAspLeuGly

RECOMBINANT GENE CODING FOR A PROTEIN HAVING ENDOCHITINASE ACTIVITY

This application is a continuation of application Ser. No. 07/842,165, filed May 1, 1992, which is a continuation of PCT/FR91/00607 Jul. 24, 1991.

FIELD OF THE INVENTION

The invention relates to a new recombinant gene coding for a new protein having endochitinase activity or for a precursor thereof, to a bacterium containing this recombinant gene, to a plant cell, a plant or a plant part, especially a plant seed, which contain a recombinant gene of this type, and to a method for rendering plants resistant to pathogenic agents such as fungi and bacteria as well as arthropods, in particular insects, and nematodes, which comprises a step of transformation with this gene, as well as to this new protein and to a method for preparing it.

Crop plants are subjected to attacks by pathogenic agents such as fungi and bacteria, which are responsible for substantial harvest losses. At present, the principal means of controlling these agents lies in the use of chemical substances having fungicidal or bactericidal activity. It is now known that plants react naturally to such attack by various defence mechanisms, which are unfortunately in general triggered too late and at too low an intensity to be sufficiently effective. One of these mechanisms comprises the induction of an enzyme known as chitinase EC 3.2.1.14 (A. Toppan et al., 1982, Agronomie, 2, 829–834). This induction may be artificially stimulated with substances such as ethylene, and results in an increase in resistance of the treated plant to pathogenic agents (Boller T., 1988, Oxford Surveys of Plant Molecular and Cell Biology, 5, 145–174).

Chitin is a linear polysaccharide polymer consisting of N-acetylglucosamineB units linked via β-(1→4) bonds. It is a structural compound present in the walls of most pathogenic fungi, in the exoskeleton of arthropods, especially insects, and in the external sheath of the eggs and cysts of nematodes. The enzymes known as chitinases are capable of degrading chitin. Among these, two different groups are distinguished, defined according to their mode of attack of chitin: exochitinases capable of liberating the N-acetylglucosaimine unit located at the non-reducing ends of the chains, and endochitinases capable of fragmenting the chains, which are the only chitinases capable of inhibiting in vitro the growth of mycelial hyphae (Roberts W. K. et al., 1988, Gen. Microbiol., 134, 169–176). The great majority of known plant chitinases are of the endo type, in contrast to the known bacterial chitinases which are of the exo type (Roberts W. K. et al., 1988, Gen. Microbiol., 134, 169–176).

A large number of plant endochitinases, in particular those of tomato and tobacco (P. AUDY et al., 1990, Phytochem, 29, 4, 1143–1159), also exhibit a lysozyme activity, a capacity to cleave the β-(1→4) bonds between the N-acetylglucosamine and the N-acetylmuramic acid of the peptidoglycan of bacterial walls. It may hence be acknowledged that lysozyme and endochitinase activities are fairly closely related (Roberts W. K. et al., 1988, Gen. Microbiol., 134, 169–176), and that a new protein having endochitinase activity, especially one of structures intermediate between tomato endochitinase and tobacco endochitinase, probably exhibits lysozyme activity.

DNA sequences coding for bacterial exochitinases have already been isolated and cloned (Jones J. D. G. et al., 1986, EMBO J., 5, 467–473 and Sundheim L. et al., 1988, Physiol. Molec. Plant Pathol., 33, 483–491). U.S. Pat. No. 4,751,081 describes the isolation and cloning of the complete gene coding for *Serratia marcescens* chitinase, as well as the transformation of *Pseudomonas fluorescens* NZ130 and *Pseudomonas putida* MK280 bacteria with this gene. These transformed bacteria are capable of slightly degrading a colloidal chitin dispersed in the bacterial culture medium. The work of Harpster M. H. et al., 1989, Nucl. Ac. Res., 17, 5395 has shown that this gene codes for an exochitinase, thereby explaining the low efficiency of degradation observed (see Table 2, col. 13 and 14 of this document). The publication of Jones J. D. G. et al., (1988), Mol. Gen. Gen,et., 212, 536–542, mentions the transformation of tobacco plants with *Agrobacterium tumefaciens* containing a chimeric gene comprising the coding portion of *Serratia marcescens* exochitinase under the control of different plant promoters. This document gives no information about the possible increase in resistance to pathogens conferred by the expression of this exochitinase.

Genomic DNA and/or complementary DNA sequences coding for some plant endochitinases have, moreover, been isolated and cloned (Broglie K. E., 1986, Proc. Ntl. Acad. Sci. USA, 83, 6820–6824 and Headrick S. A., 1988, Plant Physiol., 86, 182–186).

International application WO 90/07001 discloses the construction of a plasmid bearing a cDNA of the endochitinase of bean *Phaseolus vulgaris* under the control of a strong promoter, the conversion with the aid of *Agrobacterium tumefaciens*, the regeneration of the transformed tobacco, test showing the increased resistance to fungi *Rhizoctonia solani* and *Botrytis cinerea* of the regenerated plants, the obtention of transgenic tomato plants expressing the bean chitinase as well as the obtention, by means of this gene, of colza transgenic plants having a chitinase activity and an increased resistance to *Rhizoctonia solani* with regard to the non-transformed colza plants.

SUMMARY OF THE INVENTION

The invention hence relates to a new recombinant gene, characterized in that it codes for a protein having endochitinase activity or a precursor thereof which comprises the sequence (1) below (SEQ ID NO: 1)

Gly Gly Asp Leu Gly Ser Val Ile Ser Asn Ser Met Phe Asp
Gln Met Leu Lys His Arg Asn Glu Asn Ser Cys Gln Gly
Lys Asn Asn Phe Tyr Ser Tyr Asn Ala Phe Ile Thr Ala
Ala Arg Ser Phe Pro Gly Phe Gly Thr Ser Gly Asp Ile
Asn Ala Arg Lys Arg Glu Ile Ala Ala Phe Phe Ala Gln
Thr Ser His Glu Thr Thr Gly Gly Trp Pro Ser Ala Pro
Asp Gly Pro Phe Ala Trp Gly Tyr Cys Phe Leu Arg Glu
Arg Gly Asn Pro Gly Asp Tyr Cys Ser Pro Ser Ser Gln
Trp Pro Cys Ala Pro Gly Arg Lys Tyr Phe Gly Arg Gly
Pro Ile Gln Ile Ser His Asn Tyr Asn Tyr Gly Pro Cys
Gly Arg Ala Ile Gly Val Asp Leu Leu Asn Asn Pro Asp
Leu Val Ala Thr Asp Pro Val Ile Ser Phe Lys Thr Ala
Ile Trp Phe Trp Met Thr Pro Gln Ser Pro Lys Pro Ser
Cys His Asp Val Ile Ile Gly Arg Trp Asn Pro Ser Ala
Gly Asp Arg Ser Ala Asn Arg Leu Pro Gly Phe Gly Val
Ile Thr Asn Ile Ile Asn Gly Gly Leu Gly Cys Gly Arg
Gly Asn Asp Asn Arg VaL Gln Asp Arg Ile Gly Phe Tyr
Arg Arg Tyr Cys Gly ILe Leu Gly Val Ser Pro Gly Asp
Asn Leu Asp Cys Gly Asn Gln Arg Ser Phe Gly Asn
Gly Leu Leu Val Asp Thr Met

This recombinant gene preferably codes for a protein which comprises, immediately upstream of the sequence (1), the sequence (2) below (SEQ ID NO: 2):

Gln Asn Cys Gly Ser Gln Gly Gly Gly Lys Val Cys Ala
Ser Gly Gln Cys Cys Ser Lys Phe Gly Trp Cys Gly Asn

Th, Asn Asp His Cys Gly Ser Gly Asn Cys Gln Ser Gln
Cys Pro Gly Gly Gly Pro Gly Pro Gly Pro Val Thr which is designed to be cleaved off during the maturation of the protein, or a sequence exhibiting a substantial degree of homology with the sequence (2).

Preferably, this recombinant gene codes for a protein whose sequence comprises, upstream of the sequence (1) and preferably separated from the sequence (1) by a sequence designed to be cleaved off, a sequence coding for a signal peptide. An especially advantageous gene of this type is that which codes for a protein whose sequence comprises, immediately upstream of the sequence (2) or of a sequence exhibiting a substantial degree of homology with the sequence (2), the sequence (3) below (SEQ ID NO: 3):

Met Arg Arg Thr Ser Lys Leu Thr Thr Phe Ser Leu Leu
Phe Ser Leu Val Leu Leu Ser Ala Ala Leu Ala or a sequence exhibiting a substantial degree of homology with the sequence (3).

The invention also relates to a recombinant gene coding for a protein having endochitinase activity or for a precursor thereof, which comprises a sequence exhibiting a substantial degree of homology with the sequence (1). The coding portion of this recombinant gene comprises at least one portion 5' of the genomic DNA or complementary DNA of tomato endochitinase and at least one portion 3' of the genomic DNA or complementary DNA of tobacco endochitinase. Preferably, the coding portion of the recombinant gene possesses at least one intron. In effect, it is known that the presence of introns in the coding portion of a gene increases expression of the latter (see, for example, the work of J. CASSIS et al., 1987, Genes and development, 1, 1183–1200).

An example of such a recombinant gene is the recombinant gene in which the coding portion is the sequence below (SEQ ID NO: 4):

The invention also relates to a bacterium, for example of the species *E. coli*, which contains the recombinant gene defined above in a nucleotide environment or context permitting its replication and can hence be used for the cloning of this gene, as well as to a bacterium capable of infecting a plant with transfer of genetic material, for example of one of the species *Agrobacterium rhizogenes* and *Agrobacterium tumefaciens*, which contains this gene in a context permitting its replication and can hence be used for transforming plant cells. The transformation of plant cells by the above gene may also be performed by another biological method such as the pollen tube technique (Zhong-xun Luo et al., Plant Molec. Biol. Rep., 1988, 6, 165–176) and the direct transformation of germinating seeds (Toepfer R. et al., 1989, The Plant Cell., 1, 133–139), or by a physical method such as the use of polyethylene glycol, electroporation (Chistou P. et al., 1987, Proc. Ntl. Acad. Sci. USA, 84, 3662–3699) and bombardment using microprojectiles (Klein T. M. et al., 1988, Proc. Ntl. Acad. Sci. USA, 85, 8502–8505).

The invention also relates to a plant cell, characterised in that it is transformed by the recombinant gene as hereinabove defined, inserted in a context capable of permitting its expression. This plant cell can originate from a major crop species such as, for example, maize, soya bean, beet, wheat, barley, poppy, rape, sunflower, alfalfa and sorghum, from a floral species such as the rose, carnation and gerbera or from an edible species such as carrot, tomato, lettuce, chicory, capsicum, melon and cabbage. Species given particular consideration are *Brassica napus* rape, *Helianthus annuus* sunflower and *Nicotiana tabacum* tobacco.

The transformation step which involves one or a few cells is followed by a step of multiplication of transformed cells so as to obtain calluses, which can give rise to transformed plants by processes of organogenesis or embryogenesis. A part of the descendants of these transformed plants contains and expresses the recombinant gene.

| | | | | |
|---|---|---|---|---|
| ATGAGGCGAA | CTTCTAAATT | GACTACTTTT | TCTTTGCTGT | TTTCTCTGGT |
| TTTGCTGAGT | GCTGCCTTGG | CACAGAATTG | TGGTTCACAG | GGCGGAGGCA |
| AAGTTTGTGC | GTCGGACAA | TGTTGCAGCA | AATTCGGGTG | GTGCGGTAAC |
| ACTAATGACC | ATTGTGGTTC | TGGCAATTGT | CAAAGTCAGT | GTCCAGGTGG |
| CGGCCCTGGT | CCTGGTCCTG | TTACTGGTGG | GGACCTCGGA | AGCGTCATCT |
| CAAATTCTAT | GTTTGATCAA | ATGCTTAAGC | ATCGTAACGA | AAATTCTTGT |
| CAAGGAAAGA | ATAATTTCTA | CAGTTACAAT | GCCTTTATTA | CTGCTGCTAG |
| GTCTTTTCCT | GGCTTTGGTA | CAAGTGGTGA | TATCAATGCC | CGTAAAAGGG |
| AAATTGCTGC | TTTCTTTGCC | CAAACCTCCC | ATGAAACTAC | TGGTATGTGT |
| ATAACCATTC | ACATCGAACC | ATTAAAATAT | AATTTCATTT | TATTTTATTT |
| AGTAATTGAT | TATATATGTA | GGAGGATGGC | CTTCCGCACC | TGATGGACCA |
| TTCGCATGGG | GTTACTGTTT | CCTTAGAGAA | CGAGGTAACC | CCGGTGACTA |
| CTGTTCACCA | AGTAGTCAAT | GGCCTTGTGC | ACCTGGAAGG | AAATATTTCG |
| GACGAGGCCC | AATCCAAATT | TCACAGTAAG | CTACATAAAT | CTATATATGG |
| TAAAATTTGA | TGAACTTGTA | GTGTCTAATT | ACGTGTATTT | TGACATTTCA |
| AAACAGCAAC | TACAACTATG | GGCCATGTGG | AAGAGCCATC | GGAGTGGACC |
| TTTTAAACAA | TCCTGATTTA | GTAGCCACAG | ACCCAGTCAT | CTCATTCAAG |
| ACTGCTATCT | GGTTCTGGAT | GACCCCTCAA | TCACCAAAGC | CTTCTTGCCA |
| CGATGTCATC | ATTGGAAGAT | GGAACCCATC | TGCCGGTGAC | CGATCAGCCA |
| ATCGTCTTCC | TGGATTTGGT | GTCATCACAA | ACATCATCAA | TGGGGGCCTG |
| GAATGTGGTC | GTGGCAATGA | CAATAGGGTC | CAGGATCGCA | TTGGGTTTTA |
| CAGGAGGTAT | TGCGGTATTC | TTGGTGTTAG | TCCTGGTGAC | AATCTTGATT |
| GCGGAAACCA | GAGATCTTTT | GGAAACGGAC | TTTTAGTCGA | TACTATGTAA |
| TGA | | | | |

This coding sequence is preferably preceded by a promoter sequence containing a strong viral promoter such as the 35S promoter of cauliflower mosaic virus (see ODELL J. T. et al., 1985, NATURE, 313, 810–812), and followed by a termination sequence containing the nopaline synthase terminator of *Agrobacterium tumefaciens* (see BEVAN M. et al., 1983, Nucl. Ac. Res., 11, 369).

The invention hence also relates to a plant or a plant part, characterized in that it contains, in a context capable of permitting its expression, the recombinant gene as hereinabove defined. A plant part given particular consideration is the seed: grain or some other part of a plant capable of forming a complete new plant, in particular after sowing or burying in the ground. These plants can be any one of the above species, and more especially of the species *Nicotiana tabacum, Helianthus annuus* and *Brassica napus*.

The invention also relates to a method for obtaining plants resistant to pathogenic agents such as fungi and bacteria as well as arthropods, especially insects, and nematodes, characterized in that it comprises a step of transformation of plant cells by the recombinant gene as hereinabove defined, followed by a step of multiplication of the transformed cells and a step of regeneration of the plants.

Preferably, the step of transformation of the plant cells is performed in vitro using an agrobacterium (that is to say a bacterium of the genus Agrobacterium) which has integrated the recombinant gene as hereinabove defined.

The invention also relates to the plants resistant to pathogenic agents, capable of being obtained using the method defined above.

The invention also relates to the use of a plant falling within the category of the plants defined in the preceding paragraph, or of a plant containing, in a context capable of permitting its expression, the recombinant gene as hereinabove defined, as a parent in a selection programme for creating new plant varieties.

The invention also relates to a new protein having endochitinase activity which comprises the sequence (1), as well as to a method for obtaining it which comprises the culturing of plant cells or calluses transformed by the recombinant gene, lysis of these cells or calluses, and isolation and purification of the recombinant protein. This protein can be of interest as an active principle of a new medicinal product intended for treating conditions such as, for example, mycoses.

A better understanding of the invention will be gained from the examples below:

A large part of the collective techniques below, which are well known to those skilled in the art, is described in detail in the work by Maniatis et al. "Molecular cloning: a laboratory manual" published in 1989 by Cold Spring Harbor Press publications, New York (2nd edition).

The biological material (strains, phages, plasmids or plants) used in the examples below is commercially available and described, respectively, in the documents below:

phage lambda CHARON 4A: MANIATIS et al. Op. Cit.

shuttle vector pBIN19: BEVAN et al., 1984, Nucl. Ac. Res., 12, 8711–8721;

plasmide pBI121: JEFFERSON R. A. et al., 1987, E.M.B.O.J., 6, 3901;

*E. coli* strain MC1061: MEISSNER P. S. et al., 1987, Proc. Natl. Acad. Sci. USA, 84 4171;

*E. coli* strain HB101: MANIATIS et al., Op. Cit.;

*Agrobacterium tumefaciens* strain LBA4404: HOEKEMA et al., 1983, NATURE, 303, 179–180;

*Nicotiana tabacum* plant var. Wisconsin Havana 38: SCHNEIDER M., 1990, Plant Molec. Biol., 14, 935–947;

*Chalara elegans* fungus: RAWLINGS R. E., 1940, Ann. Mo-Bot. Gdn., 27, 561–598;

*Nicotiana tabacum* plant var. Paraguay 49 obtained from the Tobacco Institute, Bergerac, France.

*Alternaria brassicae* fungus: BAINS and TEWARI Physiol. Mol.Plant. Pathol. 30, 259, 1987

*Helianthus annuus* plant: Euroflor variety of RUSTICA seeds

*Sinapis alba*: BAIN and TEWARI above cited reference

The following abbreviations are used in the examples below:

alpha32-dCTP: deoxycitidine 5'-[alpha-$^{32}$P]triphosphate marketed boy AMERSHAM under the reference 10205;

0.2×SSC: 30 mM NaCl, 3 mM trisodium citrate pH 7.0 (described by MANIATIS et al., op. cit.);

SDS: sodium dodecyl sulphate;

FPLC: fast protein liquid chromatography;

PVDF: polyvinylidene difluoride.

BRIEF DESCRIPTION OF THE DRAWINGS

FIG. 2 (SEQ ID NO: 5) represents the genomic DNA sequence, and the deduced peptide sequence (SEQ ID NO: 6), of endochitinase of tomato having 3.5 k$^b$ s, inserted into plasmid pCH3.5.

FIG. 3 represents the alignment on the basis of maximum homology of tomato endochitinase genomic DNA devoid of introns (lower line (SEQ ID NO: 14)) and tobacco endochitinase complementary DNA (upper line (SEQ ID NO: 15)).

FIG. 4 (SEQ ID NO: 12) represents the coding sequence of the chimeric gene flanked by the BamHI and SacI sites, and the deduced amino acid sequence (SEQ ID NO: 13).

FIG. 5 (SEQ ID NO: 9) represents the sequence of the complete chimeric gene.

FIG. 6 (SEQ ID NO: 1) represents the sequence of the mature recombinant endochitinase.

DETAILED DESCRIPTION OF THE INVENTION

EXAMPLE 1

Figure 1:
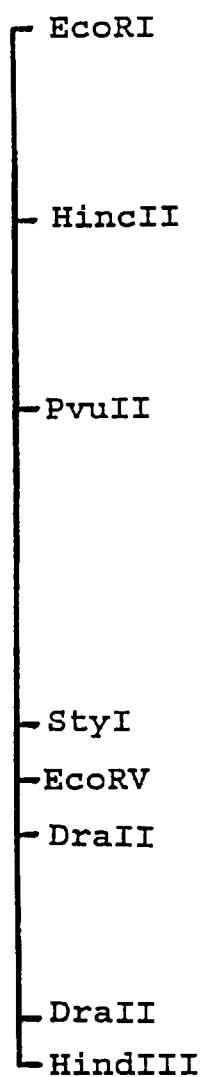
FIG. 1 represents a restriction map of the genomic DNA fragment of tomato endochitinase, having 3.5 kbs, inserted into plasmid pCH3.5.

Construction of the shuttle vector pBR1 containing a tomato-tobacco recombinant gene for endochitinase 1) Preparation of the coding sequence of the recombinant gene a) Preparation of the 5' portion of the coding sequence of the recombinant gene from tomato endochitinase gDNA (genomic DNA):

A clone containing tomato endochitinase gDNA was obtained in the following manner (see Doctoral Thesis, special field: plant molecular biology, 1986, of M. DURANT-TARDIF —Paris Sud University):

A tomato genomic DNA library was constructed in phage lambda Charon 4A by cloning fragments emanating from the partial digestion with EcoRI endonuclease of *Lycopersicon esculentum* tomato genomic DNA. When the genomic library had been amplified, 6.6×10$^5$ clones were screened after transfer of the phage DNA onto nitrocellulose by techniques well known to those skilled in the art (Maniatis et al., Molecular cloning: a laboratory manual, Cold Spring Harbor Laboratory, 1984) using a cDNA probe coding for a bean endochitinase (Broglie et al., 1986, PNAS, 83, 6820–6824).

The clone, referred to as clone 10.2, which hybridises with this probe contains a 3.5-kb tomato genomic DNA fragment containing a portion of the tomato endochitinase gene. This fragment was then inserted into plasmid pEMBL8 (Dente et al., (1983), Nucl. Ac. Res., 11, 1645–1655) between the EcoRI and HindIII sites. The plasmid obtained, referred to as pCH3.5, was cloned into *E. coli*. This plasmid was then extracted and purified by the alkaline lysis method (BIRNBOIM and DOLY in Maniatis et al., op. cit.).

The use of several restriction endonucleases made it possible to establish the restriction map of the approximately 3.5-kb genomic DNA fragment inserted into plasmid pCH3.5, shown in FIG. 1.

The various EcoRI-HincII, HincII-PvuII, PvuII-EcoRV and EcoRV-HindIII fragments were prepared by digestion with the corresponding endonucleases, and were purified by agarose gel electrophoresis and isolated by electroelution (Maniatis et al., op. cit.). Each of these fragments was cloned into the DNA of the replicative form of the single-stranded phage M13mp19 (Pharmacia) between the compatible restriction sites. These fragments were then sequenced according to the dideoxyribonucleotide method (Sanger et al., PNAS-USA, 14, 5463–5467, 1977).

The sequence (SEQ ID NO: 5), as deduced from the above experiments, is shown in FIG. 2, which also indicates the restriction sites used for cloning into pEMBL8 and the important restriction sites for the next steps of the construction. The translated amino acid sequence is also shown in this figure on the line below the coding sequence, the introns being hatched.

between the coding portion, incomplete in its 3' region, of the clone pCH3.5 and the published sequence of tobacco endochitinase cDNA comprising 329 amino acids (Hideaki Shinshi et al. (1987), Proc. Ntl. Acad. Sci. USA, 84, 89–93 and (1990) Plant Mol. Biol.,, 14, 357–368) shows a substantial homology between the sequences, especially in the 3' portion of the latter (see FIG. 3, which shows an alignment performed with this software on the basis of maximum homology of these two sequences, that of the tomato endochitinase gDNA devoid of its introns being located on the lower line).

Oligonucleotides synthesised on an Applied Biosystems 4600 DNA synthesiser were assembled so as to obtain a fragment, referred to as fragment 2, whose sequence reproduces, in respect of 71 nucleotides, the tomato endochitinase gDNA sequence located downstream of the DraII site (2), and in respect of 92 nucleotides, a sequence closely resembling the 3' portion of the published sequence of tobacco endochitinase cDNA, to which a second stop codon and the sequence of the SacI restriction site have been added. This sequence is shown below: the sequence closely resembling the 3' portion of the tobacco endochitinase cDNA sequence being underlined and the SacI site being indicated (SEQ ID NO: 8)

This sequence possesses a promoter portion of 1940 nucleotides followed by a coding portion, coding for 302 amino acids, in which two introns are inserted. This coding portion is incomplete in its 3' region (no stop codon).

By the use of the StyI (position 2006) and HindIII (position 3007) restriction sites, a 1001-bp fragment was obtained; it was purified by electrophoresis on low-melting temperature agarose gel. Chemical synthesis of a 71-bp oligonucleotide, referred to as fragment 1, whose sequence is given below, enabled the 5' portion removed upstream of the StyI site to be re-formed and a BamHI restriction site to be inserted upstream of the translation initiation ATG codon. The 1071-bp BamHI-HindIII fragment was subcloned into the vector pUC 19 (Pharmacia) in the corresponding sites using T4 DNA ligase. The plasmid obtained is referred to as pCH1.

Plasmid pCH1 was subjected to a partial hydrolysis with the restriction enzymes BamHI and DraII, and a 999-bp fragment, referred to as fragment 3, whose ends consist of the BamHI site at the 5' end and the DraII site (2) at the 3' end (see FIG. 2), was then isolated and purified after agarose gel electrophoresis; the fragments 2 and 3 were ligated using T4 DNA ligase in plasmid pUC 19 opened at the BamHI and SacI restriction sites. The plasmid obtained is referred to as pCH1.2. It was checked by sequencing that the BamHI-SacI portion of this plasmid contained the expected sequence. The latter, as well as the deduced amino acid sequence, is shown in FIG. 4. This sequence comprises the coding sequence of the chimeric gene flanked by the BamHI and SacI restriction sites. This sequence codes for a protein of 329 amino acids comprising an assumed signal peptide of 24 amino acids (determined using a software which employs the method described by G. von Heijne, 1986, Nucl. Ac.

Sequence of the fragment 1: (SEQ ID NO: 7):

BamHI
↓
GGATCCATGAGGCGAACTTCTAAATTGACTACTTTTTCTTTGCTGTTTTCTGGTTTTGCTGAGT-
GCTGC b) Preparation of the Lacking 3' portion of the coding sequence of the chimeric gene:

A comparison of sequences using suitable software (University of Wisconsin software UWGCG: Devereux et al., 1984, Nucl., Ac. Res., 12, 8711–8721 - Option GAP: optimal alignment of sequences according to the method of Needleman and Wunsch, 1970 J. mol. Biol., 48, 443–453)

Res., 14, 483–490). The expected molecular mass on the basis of the sequence of this protein when its assumed signal peptide has been cleaved off is approximately 32 kDa.

2) Preparation of the complete chimeric gene and cloning of the latter into the shuttle vector pBIN 19.

The coding sequence obtained above was inserted between a promoter sequence comprising the so-called 35S promoter of cauliflower mosaic virus (35S CaMV) and a termination sequence comprising the nopaline synthase (NOS) terminator of *Agrobacterium tumefaciens*.

a) Preparation of the promoter sequence comprising the 35S promoter of cauliflower mosaic virus:

Starting with plasmid pBI121 (Clontech), by cleavage using HindIII and BamHI endonucleases followed by electrophoresis, the approximately 900-bp HindIII-BamHI fragment containing the 35S promoter is isolated. This fragment is recut with HindII. The approximately 410-bp fragment carrying the BamHI site is treated with T4 DNA ligase in the presence of a HindIII linker (synthetic sequence containing a HindIII site). After cleavage with HindIII endonuclease and electrophoresis, the resulting HindIII-BamHI fragment (of approximately 420-bp) is isolated and purified.

b) Preparation of the termination sequence comprising the nopaline synthase (NOS) terminator of *Agrobacterium tumefaciens*.

Starting with plasmid pBI121 (Clontech), by cleavage using the restriction enzymes SacI and EcoRI followed by agarose gel electrophoresis, an approximately 250-bp fragment containing the nopaline synthase terminator was isolated.

The promoter sequence, the coding sequence of the chimeric gene for chitinase and the termination sequence were ligated using T4 DNA ligase in the shuttle vector pBIN19 opened using HindIII and EcoRI endonucleases. The portion of this vector which may be transferred to plants comprises a canamycin resistance gene immediately upstream of the complete chimeric gene (see BEVAN (1984), Nucl. Ac. Res., 12, 8711–8721). The canamycin resistance gene will serve as a selection marker during the steps of transformation and analysis of the progeny of the transformed plants.

The vector obtained is referred to as pBR1. The sequence of the complete chimeric gene (SEQ ID NO: 9) checked by sequencing, is shown in FIG. 5. The plasmid is cloned into *E. coli* strain MC1061 (Clontech).

EXAMPLE 2

Transfer into *Agrobacterium tumefaciens* or *Agrobacterium rhizogenes* of plasmid pBR1 containing the tomato-tobacco chimeric gene for endochitinase a) Transfer into *Agrobacterium tumefaciens*

This transfer is carried out as described below by triparental conjugation between *E. coli* strain MC1061 containing the vector pBR1 and *Agrobacterium tumefaciens* strain LBA4404 (Clontech) using *E. coli* strain HB101 containing the mobilisation plasmid pRK2013.

*E. coli* strain MC1061 containing plasmid pBR1 and an *E. coli* strain HB101 (Clontech) containing the mobilisation plasmid pRK2013 are cultured at 37° C. in Luria medium (Gibco) in the presence of 25 mg/l of canamycin.

*Agrobacterium tumefaciens* strain LBA4404 is cultured at 28° C. in Luria medium in the presence of 100 mg/l of rifampicin (it is resistant to this antibiotic); 200 µl of each of the three cultures are mixed, plated on Luria agar medium (Gibco) and incubated over-night at 28° C. The bacteria are then resuspended in 5 ml of Luria medium and aliquot portions are plated on Petri dishes containing an agar minimum medium (described in "Plant molecular biology manual" GELVIN et al., Kluwer Academic Press, 1988) in the presence of 100 mg/l of rifampicin and 25 mg/l of canamycin. Under these conditions, only the *Agrobacterium tumefaciens* colonies which have integrated the plasmid pBR1 grow. These colonies contain the chimeric gene in a context permitting its replication.

Resistance of the selected colonies to both antibiotics is checked by subculturing these colonies on the same selection medium twice in succession. The presence of the chimeric gene for endochitinase in *Agrobacterium tumefaciens* is checked by Southern's method on a total DNA preparation. (Lysis of the cells, purification of the DNA by extraction using a phenol/chloroform mixture, according to the protocol described by GELVIN in the work cited above, cleavage of the purified DNA using restriction enzymes, agarose gel electrophoresis, transfer onto a membrane and hybridisation according to techniques well known to those skilled in the art).

b) Transfer into *Agrobacterium rhizogenes*

This transfer is carried out in the same manner as the transfer into *Agrobacterium tumefaciens* described in a), with *Agrobacterium rhizogenes* strain A4 described by GUERCHE et al. (1987) Mol. gen. genet. 206, 382.

EXAMPLE 3

Production of transformed tobacco plants

*Nicotiana tabacum* tobacco cultured in vitro was infected with *Agrobacterium tumefaciens* containing plasmid pBR1 according to the procedure of Horsch et al., well known to those skilled in the art (HORSCH R. B. et al. 1985, Science 227, 1229–1231), the main steps of which are described below.

Discs of leaves of axenic *N. tabacum* tobacco plants (variety Wisconsin Havana 38, sensitive to pathogenic fungi) are incubated in a culture of *A. tumefaciens* harbouring plasmid pBR1. The discs, drained on Whatman paper, were transferred onto culture media in Petri dishes in order to multiply the transformed cells so as to obtain calluses, and then to produce shoots in the presence of cefotaxime (500 µg/ml) and canamycin (100 µg/ml). The canamycin-resistant shoots were then transferred onto a medium permitting the induction of roots in the presence of cefotaxime and canamycin. The plantlets are then transplanted into pots in a substrate composed of peat and compost, and left to grow in the greenhouse. All the transformed plants (Ro generation) which survived the steps of regeneration and acclimatisation in the greenhouse proved morphologically normal and fertile. They were self-fertilised and gave seeds ($R_1$ generation).

EXAMPLE 4

Analysis of the genomic DNA of the transformed tobacco plants (Ro generation) according to the SOUTHERN Blot technique The high molecular weight genomic DNA was isolated from mature leaves of transgenic plants of the Ro generation according to the method of extraction using cetyltrimethylammonium bromide and purification by precipitation, described in the work "Plant Molecular Biology Manual" already cited.

10 µg of this genomic DNA were digested overnight at 37° C. with 20 units of the restriction enzymes HindIII and EcoRI. The restriction fragments obtained were separated by agarose gel (1%) electrophoresis. The DNA was transferred according to the SOUTHERN Blot method onto a nitrocellulose filter and hybridised with a nucleotide probe comprising the sequence of the recombinant chimeric gene labelledt with α32-dCTP by random labelling (random priming). Washing under highly stringent conditions was carried out in the presence of 0.2×SSC, 0.1% SDS at 68° C. before autoradiography. Analysis of the autoradiogram enables the following conclusions to be drawn:

some plants do not possess copies of the transferred gene (absence of signal).

most of the plants tested contain at least one copy without rearrangement of the construction: CaMV 35S promoter—endochitinase chimzeric gene—NOS terminator.

some profiles suggest that there are internal rearrangements in construction, but these events are rare.

EXAMPLE 5

Determination for the transformed tobacco plants (Ro, $R_1$, and $R_2$ generations) of the expression of the recombinant endochitinase 1) Analysis of the messenger RNA according to the Northern Blot technique.

The total RNA of the transformed plants of the Ro generation was isolated according to the protocol of VERWOERD et al., NAR, 17, 2362, 1989. Portions of leaves are removed and ground, then treated with a phenol/Tris-HCl pH 8.0/0.1M LiCl mixture.

The RNAs are purified by treatment with chloro-form and then with 2M LiCl and precipitated.

15 μg of RNA of each plant are separated by agarose gel (1.2%) electrophoresis under denaturing conditions (Maniatis op. cit.) and then transferred onto a nitrocellulose membrane (Hybond C-extra Amersham). The messenger RNAs (mRNAs) corresponding to the gene introduced are identified using an oligonucleotide probe of sequence (SEQ ID NO: 10)

5' AGGGCCGCCACCTGGACACTGA 3' labelled beforehand by means of α32-dCTP, and terminal transferase (Boehringer Mannheim) according to the protocol described in Maniatis et al. (op. cit.).

This analysis enabled the presence of a hybridisation signal corresponding to a messenger RNA of approximately 1,500 nucleotides, absent from the untransformed plants, to be detected for the transformed plants.

2) Determination of the expression of the endochitinase.

The method used employs visualisation of the recombinant endochitinase by immunological techniques.

a) Preparation of antibodies: a tomato endochitinase was purified to homogeneity from tomato calluses as described below: tomato calluses were cultured in vitro on a Murashige and Skoog medium (Murashige T. and Skoog F., 1962, Physiol. Plant., 15, 473–497) containing 0.1 mg/l of NAA (naphthaleneacetic acid) and 1 mg/l of BAP (benzylaminopurine).

Cell extracts are obtained by grinding the plant material in a 50 mM Tris-HCl buffer solution pH 8.4 containing 15 mM β-mercaptoethanol and 5% of polyvinyl-pyrrolidone.

The protein is purified from this extract by ammonium sulphate precipitation, liquid chromatography according to the FPLC technique of PHARMACIA on the cation exchange column based on synthetic polymer (Mono S of Pharmacia) and exclusion chromatography (molecular sieving) on a crosslinked agarose according to the protocol described below:

Protocol for purification of tomato endochitinase

STEP 1

The protein extract is precipitated with ammonium sulphate (60% saturation). The proteins which have precipitated are recovered by centrifugation (15,000 g for 30 min), solubilised in a buffer solution (100 mM ammonium acetate pH 5.2) and dialysed overnight at 4° C. against 100 mM ammonium acetate buffer solution pH 5.2

Immediately before proceeding, the concentration of the buffer solution in the protein extract is brought down to 10 mM by passage through ready-to-use minicolumns (PD10, Pharmacia).

STEP 2

The protein extract is then purified by ion exchange chromatography based on synthetic polymer (Mono-S column of Pharmacia) using an FPLC technique (Pharmacia).

The extract is placed on the Mono-S column equilibrated with 10 mM ammonium acetate buffer pH 5.2. The proteins retained on the column are eluted with a linear gradient from 10 to 500 mM ammonium acetate.

STEP 3

The fractions containing tomato endochitinase are concentrated by ultrafiltration on a Centricon 10 membrane (Amicon). Purification of the protein is continued by chromatography (molecular sieving) on a crosslinked agarose (SUPEROSE 12 column, Pharmacia); elution is carried out with 500 mM ammonium acetate buffer solution pH 5.2.

At each step, the tomato endochitinase is identified by its molecular weight (polyacrylamide gel electrophoresis in the presence of SDS—visualisation with silver), and its endochitinase activity measured by a radiochemical method (see Example 9 below) using labelled chitin as substrate (MOLANO et al. (1977) Anal. Biochem 83, 648–656).

25 μg of tomato endochitinase were then injected into rabbits in 500 μl of Freund's complete adjuvant.

Three booster injections of 25 μg in Freund's incomplete adjuvant (500 μl) were carried out at 3-week intervals. The immune serum was drawn after the last injection.

b) Preparation of crude protein extracts of transformed tobacco plants (Ro generations:

The crude protein extracts were prepared from various tissues of the plant (root, stem, leaf, and the like). The tissue fragments were frozen in liquid nitrogen, reduced to powder and stored at −20° C. The powder was extracted at 4° C. in the presence of 0.1M ammonium acetate buffer pH 5.2 and subjected to centrifugation at 10,000 g. The concentration of total proteins was determined on the supernatants, hereinafter referred to as the crude protein extracts, according to the technique of Bradford (Bradford, M. M., (1976) Anal. Biochem., 72, 248–254).

c) Detection by immunoblotting (WesternBlot.)

The crude protein extracts of various transformed plants and untransformed plants (controls) were subjected to Western Blot, a technique well known to those skilled in the art and described, in particular, by H. TOWBIN et al.: Proc. Ntl. Acad. Sci. USA, 76, 1972, 4350–4354, which comprises the following steps:

denaturation by boiling for 10 min in a buffer, designated loading buffer, consisting of 0.125M Tris-HCl pH 6.8, 4% SDS, 0.002% bromophenol blue, 20% glycerol and 10% β-mercaptoethanol, according to the protocol described by LAEMMLI (U. K. LAEMMLI, Nature, 227 (1970), 680–685);

electrophoretic separation of the different proteins contained in the solubilisate according to the protocol described by LAEMMLI (U. K. LAEMMLI, Nature, 227 (1970), 680–685);

electrotransfer of the said proteins contained in the gel onto a PVDF membrane (according to the technique of H. TOWBIN et al. Proc. Natl. Acad. Sci. USA 76 (1979) 4350–4354.

Immunodetection is carried out according to a protocol comprising the following steps:
- saturation of the PVDF membrane onto which the proteins have been transferred by incubation for at least 2 hours at 37° C. in a 3% gelatin solution
- 3 washes in phosphate-buffered saline containing 0.05% of Tween 20 detergent
- incubation (1 hour at 37° C.) in the presence of the immune serum prepared above (containing polyclonal antibodies recognising the recombinant protein), diluted to 1/10,000 in phosphate-buffered saline
- 3 washes in phosphate-buffered saline containing 0.05% of Tween 20 detergent.

The antigen-antibody complex is then visualised using a streptavidin-biotin system conjugated to alkaline phosphatase with AMERSHAM kit BN 23 (Blotting-detection kit) used according to the manufacturer's directions.

The blot obtained shows the presence of a protein of approximately 26 kDa for the transformed plants, absent from the control plants. (The protein deduced from the sequence of the chimeric gene, when its assumed signal peptide has been cleaved off, has a molecular mass of approximately 32 kDa).

Analysis according to the Northern Blot technique and according to the Western Blot technique was performed on 30 transformed plants (responding positively to Southern Blot). 28 plants showed an expression of the messenger RNA of the chimeric gene in Northern Blot and an expression of the recombinant endochitinase in Western Blot. The non-expression in the case of 2 plants probably results from insertion of the chimeric gene in an untranscribed context.

Analysis according to the Northern Blot technique and according to the Western Blot technique was also performed on the plants of the $R_1$ generation derived from transformed plants of the Ro generation expressing the recombinant protein, and on plants of the $R_2$ generation derived from plants of the $R_1$ generation expressing the recombinant protein. In keeping with Mendelian segregation (see Example 6 below), most but not all of the plants of the $R_1$ generation and of the $R_2$ generation express the recombinant protein.

These results hence show the stability of the insertion of the gene in the tobacco plants, and of its expression during successive generations.

EXAMPLE 6

Genetic analysis of the transformed tobacco plants ($R^1$ generation)

Tobacco plants regenerated (Ro generation) in the presence of canamycin were self-pollinated. The mature seeds ($R_1$ generation) are harvested and stored in Eppendorf tubes at 4° C. The seeds are surface-sterilised using 2% aqueous calcium hypochlorite solution. The seeds are then rinsed with sterile water, dried for 24 h in a laminar-flow hood on filter paper and left to germinate on Murashige and Skoog agar medium supplemented with 100 µg/ml of canamycin (the Kanamycin resistance gene linked to the complete chimeric gene and transferred to the tobacco plant at the same time as the latter serves here as a selection marker).

Genetic analysis was performed on the progeny of 16 transformed plants (of the Ro generation) chosen from the 28 plants expressing the recombinant endochitinase (see Example 4), designated by the abbreviation Tn (n being the No. assigned to the plant) and of one untransformed control *Nicotiana tabacum* var. Wisconsin Havana 38 plant, designated by the abbreviation WH 38.

The number of individuals observed (total population) varies according to the progeny from 27 to 139. The germination rate is high (of the order of 95%), and comparable for all the plants studied.

Two types of phenotypes are observed at the time of germination of the seeds:
- Kanamycin-resistant plantlets which grow well in the presence of 100 µg/ml of canamycin and possess a developed root system and green leaves,
- Kanamycin-sensitive plantlets, corresponding either to plants which do not develop roots and which produce white leaves, or to plants for which the root system is reduced and which produce leaves with white areas.

The genetic segregation is defined as the ratio of the number of plants resistant to the number of plants sensitive to Kanamycin.

Table 1 below collates the results obtained:

TABLE 1

SEGREGATIONS OBSERVED IN THE PROGENY OF TRANSFORMED TOBACCO PLANTS AND INTERPRETATION

|  | PLANT | $Km^r$ $Km^s$ observed populations | | Total populations | Tested theoretical segregation | $Km^r$ $Km^s$ theoretical populations | | Chi Square | Conclusion: actual segregation |
|---|---|---|---|---|---|---|---|---|---|
| Transformed plants | T1 | 62 | 27 | 89 | 3:1 | 66.75 | 22.25 | 1.35 | 3:1 |
|  | T2 | 66 | 14 | 80 | 3:1 | 60 | 20 | 2.40 | 3:1 |
|  | T4 | 66 | 25 | 91 | 3:1 | 68.25 | 22.75 | 0.30 | 3:1 |
|  | T6 | 86 | 5 | 91 | 15:1 | 85.31 | 5.69 | 0.09 | 15:1 |
|  | T11 | 48 | 11 | 59 | 3:1 | 44.25 | 14.75 | 1.27 | 3:1 |
|  | T12 | 61 | 31 | 92 | 3:1 | 69 | 23 | 3.71 | 3:1 |
|  | T14 | 85 | 3 | 88 | 15:1 | 82.5 | 5.5 | 1.21 | 15:1 |
|  | T16 | 73 | 21 | 94 | 3:1 | 70.5 | 23.5 | 0.35 | 3:1 |
|  | T19 | 74 | 19 | 93 | 3:1 | 69.75 | 23.25 | 1.04 | 3:1 |
|  | T27 | 35 | 13 | 48 | 3:1 | 36 | 12 | 0.11 | 3:1 |
|  | T28 | 51 | 19 | 70 | 3:1 | 52.5 | 17.5 | 0.17 | 3:1 |
|  | T29 | 59 | 26 | 85 | 3:1 | 63.75 | 21.25 | 1.42 | 3:1 |
|  | T30 | 17 | 10 | 27 | 3:1 | 20.25 | 6.75 | 1.59 | 3:1 |

TABLE 1-continued

SEGREGATIONS OBSERVED IN THE PROGENY OF TRANSFORMED TOBACCO PLANTS AND INTERPRETATION

|  | PLANT | $Km^r$ observed populations | $Km^s$ observed populations | Total population | Tested theoretical segregation | $Km^r$ theoretical populations | $Km^s$ theoretical populations | Chi Square | Conclusion: actual segregation |
|---|---|---|---|---|---|---|---|---|---|
|  | T31 | 139 | 0 | 139 | — | — | — | — | >2loci |
|  | T36 | 65 | 25 | 90 | 3:1 | 67.50 | 22.50 | 0.37 | 3:1 |
|  | T37 | 71 | 25 | 96 | 3:1 | 72 | 24 | 0.06 | 3:1 |
| Control plant | WH138 | 0 | 89 | 89 | — | — | — | — | — |

WH38: untransformed *Nicotiana tabacum* var. Wisconsin Havana 38 plant
Tn: progeny of the transformed plant expressing the recombinant endochitinase
$Km^r$: number of Kanamycin-resistant plants; Khi-2 at the 5% level = 3.84
$Km^s$: number of Kanamycin-sensitive plants
When the observed Khi-2 is less than 3,84, the observed and assumed segregations coincide.

Statistical analysis of the results collated in Table 1 above shows that the character of canamycin resistance, genetically linked to the character conferred by the endochitinase chimeric gene, behaves as a single dominant Mendelian character (Mendelian segregation 3:1 or 15:1) present at a single :Locus ( one or several similar copies of the gene T1, T2, T4, T11, T12, T16, T.19, T27, T28, T29, T30, T36 and T37—3:1), at two loci (two assemblies genetically far apart each comprising one or several genetically similar copies of the gene T6 and T14 15:1) or at more than two loci (in the case of the plant T31).

The number of loci in each plant was confirmed by analysis of the progeny of the $R_2$ generation.

EXAMPLE 7

Measurement of the resistance of the transformed plants ($R_1$ generation) to pathogenic fungi Canamycin-resistant plantlets of the $R_1$ generation derived from the 16 chosen transformed plants, from one *Nicotiana tabacum* var. Wisconsin Havana 38 plant sensitive to *Chalara elepans* (also known as *Thielaviopsis basicola*), designated by the abbreviation WH38, and from one *Nicotiana tabacum* var. Paraguay 49 plant, designated by the abbreviation P49, genetically tolerant to this fungus, were transferred to the greenhouse for assessment of their resistance to this fungus. The latter was chosen since it is representative of the pathogenic fungi of tobacco possessing chitin in their wall. The study covered populations of plantlets varying from 15 to 36 according to the plants. The protocol chosen in this study is described below:

The plantlets are cultivated in small pots (3×3 cm). On appearance of the 5th leaf, the plants are inoculated by depositing a suspension of endoconidia ($5×10^5$ spores/ml) on the hypocotyl. The endoconidia are taken from mycelia cultures of this fungus maintained on potato dextrose agar medium (Difco) at 22° C. and in darkness. Resistance to *Chalara elegans* is assessed by assigning a score 45 days after inoculation. The plants are scored according to the symptoms of infection and according to their level of vegetative development relative to an uninoculated control (this control is an uninoculated WH38 plant for the plants derived from the 16 chosen transformed plants and from the WH38 plant, and an uninoculated P49 plant for the plants derived from the P49 plant). The classes are defined according to the following criteria:

Score 0: plant dead; score 1: terminal bud still green, root system destroyed; score 2: plant development not exceeding 25% of that of the control, root system completely necrotic; score 3: plant development attaining 50% of the development of the control, root system exhibiting healthy parts; score 4: plant development identical to the control.

The index of resistance of the progeny of a transformed plant represents the mean of the scores assigned to the plantlets derived from this plant.

Table 2 below collates the results obtained.

TABLE 2

MEASUREMENT OF THE RESISTANCE OF PROGENY OF TRANSFORMED TOBACCO PLANTS TO PATHOGENIC FUNGI

|  | Plant | Population tested | Index of resistance of the progeny |
|---|---|---|---|
| Transformed plants | T1 | 32 | 2.030 |
|  | T2 | 31 | 0.065 |
|  | T4 | 36 | 1.200 |
|  | T6 | 34 | 0.743 |
|  | T11 | 35 | 2.514 |
|  | T12 | 33 | 1.632 |
|  | T14 | 26 | 1.769 |
|  | T16 | 36 | 1.750 |
|  | T19 | 36 | 1.416 |
|  | T27 | 20 | 0.050 |
|  | T28 | 27 | 1.444 |
|  | T29 | 36 | 1.750 |
|  | T30 | 15 | 2.666 |
|  | T31 | 36 | 2.888 |
|  | T36 | 36 | 1.686 |
| Control plants | WH38 | 34 | 0.044 |
|  | P49 | 34 | 2.823 |

WH38: untransformed *Nicotiana tabacum* var. Wisconsin Havana 38 plant
P39: *Nicotiana tabacum* var. Paraguay 49 plant
Tn: progeny of the transformed plant expressing the recombinant endochitinase.

It is observed on reading the above table that all the progenies of the transformed plants Tn possess an index of resistance greater than that of the progeny of the WH38 control plant (untransformed plant), and sometimes close to or even greater than that of the progeny of the genetically resistant P49 control plant.

EXAMPLE 8

Production of transformed rape plants

The transformation is carried out according to the protocol of P. GUERCHE et al. (P. GUERCHE et al. 1987, Mol.

Gen. Genet., 206, 382). The various culture media are those described by Pelletier et al. (Pelletier et al., 1983, Mol. gen. genet., 191, 244). Details of their composition will be given later (Table 3).

a) Production of transformed roots

Stem segments are removed from the apical tip of rape plants (*Brassica napus*: spring varieties Brutor and Westar and winter variety) approximately 1 m high. These segments are surface-sterilised, rinsed in sterile water, cut into segments approximately 1.5 cm long and placed in a tube containing medium A.

Inoculation of the tip of this segment is performed by depositing a suspension of the *Agrobacterium rhizogenes* strain containing plasmid pBR1.

Transformed roots appear on the stem segment after 1 to 2 weeks; they are removed and placed on medium B containing agar (15 g/l) and supplemented with 500 μg of cefotaxime/ml.

b) Production of transformed calluses

Root fragments are incubated for 15 days on medium D containing 3 mg/l of 2,4-dichlorophenoxyacetic acid, and then transferred onto the same medium containing agar (15 g/l) for the purpose of multiplication of the transformed cells so as to obtain calluses and to yield crude extracts intended for purification of the recombinant protein (see Example 10 below).

c) Regeneration of transformed plants

Root fragments are incubated for 15 days on medium D containing 3 mg/l of 2,4-dichlorophenoxyacetic acid, and then placed on RCC medium for induction of buds. Rooted plants are then obtained by transfer of the buds to media F and G.

TABLE 3

Composition of the various media used for the production of transformed rape plants

| Composition (mg/l) | Medium | | | | | |
|---|---|---|---|---|---|---|
| | A | B | D | RCC | F | G |
| NH$_4$NO$_3$ | 1,650 | | 200 | 1,650 | 1,650 | 825 |
| KNO$_3$ | 1,900 | 2,500 | 1,250 | 1,900 | 1,900 | 950 |
| (NH$_4$)$_2$SO$_4$ | | 134 | 67 | | | |
| NaH$_2$PO$_4$ | | 150 | 75 | | | |
| KH$_2$PO$_4$ | 170 | | 35 | 170 | 170 | 85 |
| CaCl$_2$.2H$_2$OO | 440 | 750 | 525 | 440 | 440 | 220 |
| MgSO$_4$.7H$_2$O | 370 | 250 | 250 | 370 | 370 | 185 |
| H$_3$BO$_3$ | 12.4 | 3 | 12.4 | 12.4 | 6.2 | 6.2 |
| MnSO$_4$.4H$_2$O | 33.6 | 10 | 33.6 | 33.6 | 22.3 | 22.3 |
| ZnSO$_4$.7H$_2$O | 21 | 2 | 21 | 21 | 8.6 | 8.6 |
| KI | 1.66 | 0.75 | 1.66 | 1.66 | 0.83 | 0.83 |
| Na$_2$MoO$_4$.2H$_2$O | 0.5 | 0.25 | 0.5 | 0.5 | 0.25 | 0.25 |
| CuSO$_4$.5H$_2$O | 0.05 | 0.025 | 0.05 | 0.05 | 0.025 | 0.025 |
| CoCl$_2$.6H$_2$O | 0.05 | 0.025 | 0.05 | 0.05 | 0.025 | 0.025 |
| FeSO$_4$.7H$_2$O | 22.24 | 27.8 | 27.8 | 27.8 | 27.8 | 22.24 |
| Na$_2$EDTA | 29.84 | 37.3 | 37.3 | 37.3 | 37.3 | 29.84 |
| Inositol | 100 | 100 | 100 | 100 | 100 | 100 |
| Nicotinic acid | 0.5 | 1 | 1 | 0.5 | 1 | 0.5 |
| Pyridoxine HCl | 0.5 | 1 | 1 | 0.5 | 1 | 0.5 |
| Thiamine | | 10 | 10 | | 10 | |
| Glycine | 2 | | | 2 | | 2 |
| Glucose | 10,000 | 20,000 | | | | 10,000 |
| Sucrose | 10,000 | | 20,000 | 10,000 | 10,000 | |
| D-Mannitol | | 70,000 | | 10,000 | | |
| NAA | | 1 | | 1 | 0.1 | 0.01 |
| BA | | 1 | | 0.5 | 0.5 | |
| 2,4D | | 0.25 | 1 | | | |
| Adenine sulphate | | | 30 | | | |
| IPA | | | | 0.5 | | |
| GA | | | | 0.02 | | |
| Tween 80 | | 10 | | | | |
| Agar | 8,000 | | | 8,000 | 8,000 | 8,000 |
| pH | 5.8 | 5.8 | 5.8 | 5.8 | 5.8 | 5.8 |
| Gentamicin (sulphate) | 10 | | | | | |

NAA = naphthaleneacetic acid
BA = 6-benzylaminopurine acid
2,4D = 2,4-dichlorophenoxyacetic acid
IPA = N$^6$-(Δ$^2$-isopentenyl)adenine
GA$_3$ = gibberellic acid
EDTA = ethylenediaminetetraacetic acid.

EXAMPLE 9

Analysis of the genomic DNA of the transformed rape plants (Ro generation) and determination for the latter and their progeny of the expression of the recombinant endochitinase 1) Analysis of the genomic DNA according to the Southern Blot technical Analysis of the genomic DNA according to the Southern Blot technique, performed under the conditions described in Example 4, enabled it to be established that most of the plants tested contain at least one copy without rearrangement of the construction CaMV 35S promoter—enochitinase chimeric gene—NOS terminator.

2) Analysis of the messenger RNA according to the Northern Blot technique

Analysis of the messenger RNA according to the Northern Blot technique, performed under the conditions described in Example 5, was performed only for a few plants, analysis according to the Western Blot technique being faster for yielding the expected information. It enabled the presence of a messenger RNA of approximately 1,500 nucleotides, absent from the untransformed plants, to be detected for the transformed plants analysed.

3) Determination of the expression of the recombinant endochitinase by Western Blot Western blot analysis, performed under the conditions and using the antibodies described in Example 5 on the crude protein extracts of transformed rape plants (prepared as described in Example 5 for the crude protein extracts of transformed tobacco plants) enabled the recombinant protein to be visualised.

The blot obtained shows the presence of a protein of approximately 26 kDa for the transformed plants, absent from the control plants (the protein deduced from the sequence of the chimeric gene, when its signal peptide has been cleaved off, has a molecular mass of approximately 32 kDa), and also the presence of a protein of approximately 38 kDa recognised by the antibodies, also present in untransformed plants. The latter protein is an endogenous endochitinase (Atta K. K. et al., 1988, Abstracts of the Second International Congress of Plant Molecular Biology, Jerusalem) which exhibits serological features in common with those of the recombinant endochitinase.

Analysis according to the Western Blot technique was performed on 42 transformed plants (responding positively to Southern Blot). 38 plants showed an expression of the recombinant endochitinase. The non-expression observed in the case of 4 plants probably results from insertion of the chimeric gene in an untranscribed context.

Analysis according to the Western Blot technique was also performed on plants of the $R_1$ generation derived from transformed plants of the Ro generation expressing the recombinant endochitinase. In keeping with the laws of genetics applying to heredity of diploids, most but not all of these plants expressed the recombinant protein.

These results show the stability of the insertion of the gene in the rape plants, and of its expression during the generations.

EXAMPLE 10

Purification of the recombinant endochitinase of transformed rape calluses (Ro generation), measurement of its enzymatic activity and determination of its amino-terminal sequence 1) Purification of the recombinant endochitinase:

The recombinant protein was purified from the crude protein extracts of transformed rape calluses, by ammonium sulphate precipitation, FPLC liquid chromatography on a cation exchange column based on synthetic polymer and exclusion chromatography (molecular sieving) on a crosslinked agarose, according to the protocol described below:

Protocol for purification of the recombinant endochitinase

STEP 1

The protein extract is precipitated with ammonium sulphate (60% saturation). The proteins which have precipitated are recovered by centrifugation (15,000 g for 30 min), solubilised in a buffer solution (100 mM ammonium acetate pH 5.2) and dialysed overnight at 4° C. against 100 mM ammonium acetate buffer solution pH 5.2

Immediately before proceeding, the concentration of the buffer solution in the protein extract is brought down to 10 mM by passage through ready-to-use minicolumns (PD10, Pharmacia).

STEP 2

The protein extract is then purified by ion exchange chromatography based on synthetic polymer (Mono-S column of Pharmacia) using an FPLC technique (Pharmacia).

The extract is placed on the Mono-S column equilibrated with 10 mM ammonium acetate buffer pH 5.2. The proteins retained on the column are eluted with a linear gradient from 10 to 500 mM ammonium acetate.

STEP 3

The fractions containing the recombinant endochitinase are concentrated by ultrafiltration on a Centricon 10 membrane (Amicon). Purification of the protein is continued by exclusion chromatography (molecular sieving) on a crosslinked agarose (SUPEROSE 12 column, Pharmacia), elution being carried out with 500 mM ammonium acetate buffer solution pH 5.2.

At each step, the tomato endochitinase is identified by its molecular weight (polyacrylamide gel electrophoresis in the presence of SDS—visualisation with silver), by its immunoblot (see Example 5 c)) and its endochitinase activity, measured by a radiochemical method described below using labelled chitin as substrate (MOLANO et al. (1977) Anal. Biochem 83, 648–656).

2) Measurement of the enzymatic activity of the recombinant endochitinase.

a) Method

The endochitinase activity is measured by a radiochemical method employing tritium-labelled chitin as substrate, according to a protocol described by MOLANO et al., 1977, Anal. Biochem 83, 648–656, summarised below.

To 50 µl of tritiated chitin (50 kBq/ml), washed beforehand by 4 successive centrifugations and renewal of the solvent, 50 µl of fraction containing the recombinant endochitinase are added, followed by 250 µl of 0.2M sodium acetate buffer solution pH 4.5. After incubation for 45 min at 20° C., the reaction is stopped by adding 100 µl of 20% trichloroacetic acid. After centrifugation (10,000 g for 10 min), the quantity of radioactivity solubilised in 100 µl of supernatant is measured by liquid scintillation.

At each step of purification according to the method described above, the recombinant protein (identified by means of its molecular weight and its positive reaction with polyclonal antibodies to tomato endochitinase) shows an endochitinase activity.

b) Results

The specific activities, measured at the end of step 1, step 2 and step 3, are 135, 7,416 and 32,193 cpm/µg of protein, respectively.

3) Determination of the amino-terminal sequence of the mature recombinant endochtitinase.

After purification of the recombinant endochitinase according to the protocol described above, sequencing of the amino-terminal end was carried out. The samples to be treated are carried to the surface of a PVDF (polyvinylidene difluoride) filter by electrotransfer according to the method described by H. TOWBIN et al., Proc. Ntl. Acad. Sci. USA (1979), 4350–4354, after polyacrylamide gel electrophoresis in the presence of SDS. The filter is introduced into a protein sequencer (model 470 A marketed by the company Applied Biosystems (USA)) equipped with a chromatograph (Applied Biosystems model 430) which analyses continuously the phenylthio-hydantoin derivatives formed, after each degradation cycle.

The amino-terminal sequence determined (SEQ ID NO: 11) is shown below, the symbol Xaa representing an undetermined amino acid:

Gly-Gly-Xaa-Leu-Gly-Ser-VaL-Ile-Ser-Asn-Xaa-Met-Phe-Xaa-Gln-Met-Leu-Lys-Xaa-Arg

It is seen that the beginning of the sequence of the mature protein (SEQ ID NO: 1) shown in FIG. 6 corresponds to the 76th amino-acid from amino-terminal methionine deduced from the sequence of the chimeric gene (SEQ ID NO: 12), such as shown in FIG. 4 and SEQ ID NOs. 12 and 13.

The protein translated from the messenger RNA encoded by the chimeric gene undergoes a cleavage of its assumed signal peptide of 24 amino acids (G. von Heijne, 1986, Nucl. Ac. Res., 14, 483–490), followed by a maturation producing the cleavage of an amino-terminal peptide of 51 amino acids.

The sequence of the chimeric gene hence contains the information necessary for the synthesis of a protein of the prepro-enzyme type, which is matured to active endochitinase.

EXAMPLE 11

Genetic analysis of the transformed rape plants ($R_1$ generation)

The regenerated rapes ($R_0$ generation) were self-pollinated. The mature seeds ($R_1$ generation) are collected and stored in bags. Seeds are then sown in boxes on vermiculite, then the young plants are replanted individually in 2-liter pots containing horticultural compost. The expression of the recombinant protein is emphasized by the Western Blot technique on young leaves (see paragraph 3 of Example 9) after extraction of the proteins according to the protocole described in Example 5b).

In accordance with the laws of genetics applying to heredity of diploids, most but not all of these plants express the recombinant protein.

The progeny of 15 of the transformed rape plants were statistically analyzed according to the protocol described in Example 7. The obtained results show that the expression character of the endochitinase chimeric gene behaves as a single dominant Mendelian character present at a single locus (12 progenies out of 15 exhibit the Mendelian segregation 3:1) or at two loci ( 3-progenies out of 15 exhibit the Mendelian segregation 15:1).

EXAMPLE 12

Measurement of the resistance of the transformed rape plants ($R_2$ generation) to pathogenic fungi The $R_1$ generation plants, expressing the recombinant protein are self-pollinated. the $R_2$ generation seeds obtained are germinated as described in Example 11.

The resistance of the rape plants expressing the recombinant protein is determined on the $R_2$ generation plants by inoculation in culture chamber using *Alternaria brassicae*, a fungus representative of the pathogenic fungi of the rape plant, according to the protocole described by Bains and Tewari, 1987, Physiol. Mol. Plant. Pathol. 30: 259 summarized hereafter.

Young rape plants, 21 days old, are inoculated with a suspension of spores deposited on the central vein of the first leaf, previously pricked with a needle. Two weeks later, the extent of the necrosis resulting from the growth of the parasitic fungus is measured.

The results obtained from the progeny of 10 transformed plants, show that the progeny of three plants exhibit a considerably increased resistance, close to that of a mustard variety *Sinapis alba*, Bains and Tewari, referenced above, genetically resistant to *Alternaria brassicae*.

EXAMPLE 13

Obtention of transformed roots of sunflower

Segments of petioles are taken from *Helianthus annuus* sunflower plants (Euroflor Rustica seeds variety between 6 and 10 weeks old. The segments are disinfected by soaking for 30 mins. in a 1% solution of calcium hypochlorite.

The segments of petioles are then placed in a tube containing a quantity of the gelose-containing Murashige and Skoog culture :medium. The inoculation of the end of these segments is carried out by depositing a suspension of the *Agrobacterium rhizogenes* strain containing the pBR1 plasmid.

Transformed roots appear on the segment of petiole after about 1 month . These roots are taken out and placed on the agar medium M (medium M to which 6 g/l of agarose have been added), containing 500 µg of cefotaxime/ml. The composition of the medium M is given hereinafter (Table 4). These roots are replanted every week for 4 weeks in the same medium. Then they are transferred on the liquid medium M, in order to obtain the production of roots in quantity sufficient to analyze the expression of the recombinant protein by the Western Blot technique according to the protocole described in paragraph 3 of Example 9. The crude protein extracts to be used for this analysis are prepared according to the technique described in Example 5. The blots obtained show the presence of a protein of expected molecular weight (26 kDa) for the transformed roots, absent from the control roots and leaves of sunflower plants (non-transformed plants).

TABLE 4

Composition of the culture medium M used for the culture of transformed roots of sunflower.

| | Composition mg/l |
|---|---|
| $NH_4NO_3$ | 330 |
| $KNO_3$ | 380 |
| $K_2PO_4$ | 170 |
| $MgSO_4$ | 370 |
| $CaCl_2$ | 440 |
| $H_3BO_3$ | 6.3 |
| $MnSO_4, 4H_2O$ | 22.3 |
| $ZnSO_4, 7H_2O$ | 1.6 |
| KI | 0.83 |
| $Na_{2M}oO_4, 2H_{2O}$ | 0.25 |
| $CuSO_4, 5H_2O$ | 0.025 |
| $CoCl2, 6H_2O$ | 0.025 |
| Pyridoxine HCl | 0.1 |
| Nicotinic acid | 0.1 |
| Glycine | 0.4 |
| Inositol | 20 |
| Thiamine | 0.02 |
| Sucrose | 30,000 |
| Iron citrate | 200 |

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
( A ) LENGTH: 254 amino acids
( B ) TYPE: amino acid
( D ) TOPOLOGY: linear (i i) MOLECULE TYPE: protein (x i) SEQUENCE DESCRIPTION: SEQ ID NO:1:

```
Gly Gly Asp Leu Gly Ser Val Ile Ser Asn Ser Met Phe Asp Gln Met
 1               5                  10                  15

Leu Lys His Arg Asn Glu Asn Ser Cys Gln Gly Lys Asn Asn Phe Tyr
             20                  25                  30

Ser Tyr Asn Ala Phe Ile Thr Ala Ala Arg Ser Phe Pro Gly Phe Gly
             35                  40                  45

Thr Ser Gly Asp Ile Asn Ala Arg Lys Arg Glu Ile Ala Ala Phe Phe
         50                  55                  60

Ala Gln Thr Ser His Glu Thr Thr Gly Gly Trp Pro Ser Ala Pro Asp
 65                  70                  75                  80

Gly Pro Phe Ala Trp Gly Tyr Cys Phe Leu Arg Glu Arg Gly Asn Pro
                 85                  90                  95

Gly Asp Tyr Cys Ser Pro Ser Ser Gln Trp Pro Cys Ala Pro Gly Arg
                 100                 105                 110

Lys Tyr Phe Gly Arg Gly Pro Ile Gln Ile Ser His Asn Tyr Asn Tyr
             115                 120                 125

Gly Pro Cys Gly Arg Ala Ile Gly Val Asp Leu Leu Asn Asn Pro Asp
     130                 135                 140

Leu Val Ala Thr Asp Pro Val Ile Ser Phe Lys Thr Ala Ile Trp Phe
145                 150                 155                 160

Trp Met Thr Pro Gln Ser Pro Lys Pro Ser Cys His Asp Val Ile Ile
                 165                 170                 175

Gly Arg Trp Asn Pro Ser Ala Gly Asp Arg Ser Ala Asn Arg Leu Pro
             180                 185                 190

Gly Phe Gly Val Ile Thr Asn Ile Ile Asn Gly Gly Leu Glu Cys Gly
         195                 200                 205

Arg Gly Asn Asp Asn Arg Val Gln Asp Arg Ile Gly Phe Tyr Arg Arg
     210                 215                 220

Tyr Cys Gly Ile Leu Gly Val Ser Pro Gly Asp Asn Leu Asp Cys Gly
225                 230                 235                 240

Asn Gln Arg Ser Phe Gly Asn Gly Leu Leu Val Asp Thr Met
                 245                 250
```

(2) INFORMATION FOR SEQ ID NO:2:

(i) SEQUENCE CHARACTERISTICS:
      (A) LENGTH: 51 amino acids
      (B) TYPE: amino acid
      (D) TOPOLOGY: linear (i i) MOLECULE TYPE: peptide (x i) SEQUENCE DESCRIPTION: SEQ ID NO:2:

```
Gln Asn Cys Gly Ser Gln Gly Gly Gly Lys Val Cys Ala Ser Gly Gln
 1               5                  10                  15

Cys Cys Ser Lys Phe Gly Trp Cys Gly Asn Thr Asn Asp His Cys Gly
             20                  25                  30

Ser Gly Asn Cys Gln Ser Gln Cys Pro Gly Gly Gly Pro Gly Pro Gly
             35                  40                  45

Pro Val Thr
     50
```

(2) INFORMATION FOR SEQ ID NO:3:

( i ) SEQUENCE CHARACTERISTICS:
    ( A ) LENGTH: 24 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:3:

Met Arg Arg Thr Ser Lys Leu Thr Thr Phe Ser Leu Leu Phe Ser Leu
1               5                   10                  15
Val Leu Leu Ser Ala Ala Leu Ala
            20

( 2 ) INFORMATION FOR SEQ ID NO:4:

( i ) SEQUENCE CHARACTERISTICS:
    ( A ) LENGTH: 1153 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:4:

```
ATGAGGCGAA CTTCTAAATT GACTACTTTT TCTTTGCTGT TTTCTCTGGT TTTGCTGAGT      60
GCTGCCTTGG CACAGAATTG TGGTTCACAG GGCGGAGGCA AAGTTTGTGC GTCGGGACAA     120
TGTTGCAGCA AATTCGGGTG GTGCGGTAAC ACTAATGACC ATTGTGGTTC TGGCAATTGT     180
CAAAGTCAGT GTCCAGGTGG CGGCCCTGGT CCTGGTCCTG TTACTGGTGG GGACCTCGGA     240
AGCGTCATCT CAAATTCTAT GTTTGATCAA ATGCTTAAGC ATCGTAACGA AAATTCTTGT     300
CAAGGAAAGA ATAATTTCTA CAGTTACAAT GCCTTTATTA CTGCTGCTAG GTCTTTTCCT     360
GGCTTTGGTA CAAGTGGTGA TATCAATGCC CGTAAAAGGG AAATTGCTGC TTTCTTTGCC     420
CAAACCTCCC ATGAAACTAC TGGTATGTGT ATAACCATTC ACATCGAACC ATTAAAATAT     480
AATTTCATTT TATTTTATTT AGTAATTGAT TATATATGTA GGAGGATGGC CTTCCGCACC     540
TGATGGACCA TTCGCATGGG GTTACTGTTT CCTTAGAGAA CGAGGTAACC CCGGTGACTA     600
CTGTTCACCA AGTAGTCAAT GGCCTTGTGC ACCTGGAAGG AAATATTTCG GACGAGGCCC     660
AATCCAAATT TCACAGTAAG CTACATAAAT CTATATATGG TAAAATTTGA TGAACTTGTA     720
GTGTCTAATT ACGTGTATTT TGACATTTCA AAACAGCAAC TACAACTATG GGCCATGTGG     780
AAGAGCCATC GGAGTGGACC TTTTAAACAA TCCTGATTTA GTAGCCACAG ACCCAGTCAT     840
CTCATTCAAG ACTGCTATCT GGTTCTGGAT GACCCCTCAA TCACCAAAGC CTTCTTGCCA     900
CGATGTCATC ATTGGAAGAT GGAACCCATC TGCCGGTGAC CGATCAGCCA ATCGTCTTCC     960
TGGATTTGGT GTCATCACAA ACATCATCAA TGGGGGCCTG GAATGTGGTC GTGGCAATGA    1020
CAATAGGGTC CAGGATCGCA TTGGGTTTTA CAGGAGGTAT TGCGGTATTC TTGGTGTTAG    1080
TCCTGGTGAC AATCTTGATT GCGGAAACCA GAGATCTTTT GGAAACGGAC TTTTAGTCGA    1140
TACTATGTAA TGA                                                       1153
```

( 2 ) INFORMATION FOR SEQ ID NO:5:

( i ) SEQUENCE CHARACTERISTICS:
    ( A ) LENGTH: 3012 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:

(A) NAME/KEY: intron
                (B) LOCATION: 2384..2462
                (D) OTHER INFORMATION: /number=1

(ix) FEATURE:
                (A) NAME/KEY: intron
                (B) LOCATION: 2617..2697
                (D) OTHER INFORMATION: /number=2

(ix) FEATURE:
                (A) NAME/KEY: CDS
                (B) LOCATION: join(1942..2383, 2463..2616, 2698..3007)

(ix) FEATURE:
                (A) NAME/KEY: sig_peptide
                (B) LOCATION: 1942..2166

(ix) FEATURE:
                (A) NAME/KEY: mat_peptide
                (B) LOCATION: join(2167..2383, 2463..2616, 2698..3007,
                        2698)

(xi) SEQUENCE DESCRIPTION: SEQ ID NO:5:

| | | | | | | |
|---|---|---|---|---|---|---|
| GAATTCATAT | TTATTTTAAA | AAAATATTTT | CAACTTCAAA | AATATATTTT | TTTCACGCCT | 60 |
| ACCCTCGACC | CCCCTCCCGC | ACCCTTACCC | GCCCTCTACC | AACCCCCCCC | CCCCCAAAAA | 120 |
| AAAATAAATT | AAAGTTTACT | TTTAAAAATA | TTTTCAACTT | CAAAATTTCA | TTTTTTTTCA | 180 |
| TCCCTACCCT | CGACCACCCC | CACCCTCCCG | CTAAAAAATA | AAAGTTTAAG | TTTGTTTTTG | 240 |
| AAAAGTATTT | TCAACTTCAA | AAATTCATTT | TTTCACCCCT | AACCTCAACC | CCCCACCCAC | 300 |
| ATTCCCACCC | CAATTTTTTT | TTTTAAGTTT | GTTGTTAAAA | AATATTTCT | ACTTCAAAAT | 360 |
| TTCATTTCAC | CCTTTCCCCC | CCCCCTCCCC | AAACCCCACC | CCACCCCCCC | ACCCCCAAA | 420 |
| AAAAATATTT | AAATTTGTTT | TTAAAAAATA | TTTTCAATTT | CAAAATTTTA | TTTTCTATTC | 480 |
| TAGTAAAAAT | AAAAGATATA | TCTCAAAAAC | ATTTTTTACT | TATTCAAAAA | CCAAACACTC | 540 |
| TTTTCCAGAA | AAAATTTCTA | TTCACCAACC | AAATATGAGA | AAATAAATCA | AAATCTAGTT | 600 |
| ATTTTAGAAA | ATGTTTTCCT | ACATATCAAA | CACACCCAAT | GTCTTCATTA | ATGTGTTCAG | 660 |
| ATTTATTTTA | TGTCAACTTG | GTCGCTATGT | TATATGAATT | AGCCACACAA | ATTCAATTTA | 720 |
| ATTGCACATT | ACCACTATTT | TGTAGTTCAC | GTAGAAATTA | AAGTTCATCA | CAACAAAATA | 780 |
| AATATTGGGC | GCACGGGCGA | CTCCCCACTA | GTATCACTCA | GAAATCACAA | TAAAGTATTA | 840 |
| AATTTTGTCA | AAATTCTTTA | TCCGTATTAA | GAAATCTTTG | AAGTCTGAAT | ACATATAAAT | 900 |
| TCATAATTCA | TAAATTTCAA | ATTTCTCTTA | GTAATTTTA | TTGAGTTATT | AATTTCATTT | 960 |
| AAACAAATTC | ATTGTACTTT | GTAAATACTC | CTAATTTGTA | TGATTTTGGA | CTCATGTAAG | 1020 |
| GAAACCTTAT | CAAATTAAGT | ATGGAGTTAA | AGGGGAAGAG | TAGAATTAGC | AGCCCAAAGA | 1080 |
| TACACTTTCA | AATTATGTAA | GTTTGACCCA | GCCTGCCCTA | TTTCTTCTAG | CACCAGCTGC | 1140 |
| TACCTTATAT | AATTACTTTA | ATTTGAAAAT | GTCATCAATA | TCATGCAAAA | TTTACCGGCC | 1200 |
| CTATTTCTTC | TAGCACTAGC | TACTACCTTA | TATAATTACT | TTAATTTGTA | AGTGTCATCA | 1260 |
| ATATCATGCA | AAATTTAGTC | AAAATATTTA | TCTCGATGTC | TTTGGTTCTC | AAATAGAGCA | 1320 |
| AATAGACTCA | GACTCGAACC | TACGCAAGTG | TAAAAGCAAG | GAATGATTAC | CAAACAAGAC | 1380 |
| AGTTCTCAAC | AAGCAACAAA | ATAAACAAGG | CAAAACTAGT | TAGAAAACGA | ATGCTATTGT | 1440 |
| CATTCCAGCC | GAACTAACAA | TAACCTACAT | ACAAACCAGT | TCAACCTTTA | GCTTACTTT | 1500 |
| TACCATTTTT | GGCTCTTTTG | TTAATTGAGA | TTTGAAATAA | ATCTCAACAA | TAATTTATTT | 1560 |
| ATGATCCACA | TGACATTAGT | CTAAGAGGTG | ATTGAACATT | ACTTGAGAGA | TATTGCTATT | 1620 |
| CGATGAGTTA | CATAGTTTTC | CACTACAAAT | TTAATTTACT | CTAACTATGA | ATATTATAAT | 1680 |

-continued

```
TTGTAGTACA GTTTTTATTT AATAGGTAAA TTTAATAAGA GTAAACAAAA AATATCCAGC         1740

AACTATAGTC TCCAGTCCAA ATTATGTAGA GAAAAGTCTG GAATAACGTC CAAAGCCGCC         1800

CGTCTCTTTT ACTTATAACT GAATTAAATT CTGGATACGA CAGGGTGGAC TATCAATTTT         1860

GTCATAAAAG TCACTGATTC CTCACAACCA CTTGCCTATA AATAGCTTTC ACTTTAGCAT         1920

TTGTTTGCCA TCACATTCAA A ATG AGG CGA ACT TCT AAA TTG ACT ACT TTT           1971
                         Met Arg Arg Thr Ser Lys Leu Thr Thr Phe
                         -75                 -70

TCT TTG CTG TTT TCT CTG GTT TTG CTG AGT GCT GCC TTG GCA CAG AAT           2019
Ser Leu Leu Phe Ser Leu Val Leu Leu Ser Ala Ala Leu Ala Gln Asn
-65             -60                 -55                     -50

TGT GGT TCA CAG GGC GGA GGC AAA GTT TGT GCG TCG GGA CAA TGT TGC           2067
Cys Gly Ser Gln Gly Gly Gly Lys Val Cys Ala Ser Gly Gln Cys Cys
            -45                 -40                     -35

AGC AAA TTC GGG TGG TGC GGT AAC ACT AAT GAC CAT TGT GGT TCT GGC           2115
Ser Lys Phe Gly Trp Cys Gly Asn Thr Asn Asp His Cys Gly Ser Gly
        -30                 -25                 -20

AAT TGT CAA AGT CAG TGT CCA GGT GGC GGC CCT GGT CCT GGT CCT GTT           2163
Asn Cys Gln Ser Gln Cys Pro Gly Gly Gly Pro Gly Pro Gly Pro Val
    -15                 -10                 -5

ACT GGT GGG GAC CTC GGA AGC GTC ATC TCA AAT TCT ATG TTT GAT CAA           2211
Thr Gly Gly Asp Leu Gly Ser Val Ile Ser Asn Ser Met Phe Asp Gln
1               5                   10                      15

ATG CTT AAG CAT CGT AAC GAA AAT TCT TGT CAA GGA AAG AAT AAT TTC           2259
Met Leu Lys His Arg Asn Glu Asn Ser Cys Gln Gly Lys Asn Asn Phe
            20                  25                  30

TAC AGT TAC AAT GCC TTT ATT ACT GCT GCT AGG TCT TTT CCT GGC TTT           2307
Tyr Ser Tyr Asn Ala Phe Ile Thr Ala Ala Arg Ser Phe Pro Gly Phe
            35              40                      45

GGT ACA AGT GGT GAT ATC AAT GCC CGT AAA AGG GAA ATT GCT GCT TTC           2355
Gly Thr Ser Gly Asp Ile Asn Ala Arg Lys Arg Glu Ile Ala Ala Phe
        50                  55                  60

TTT GCC CAA ACC TCC CAT GAA ACT ACT  G GTATGTGTAT AACCATTCAC              2403
Phe Ala Gln Thr Ser His Glu Thr Thr
            65              70

ATCGAACCAT TAAAATATAA TTTCATTTTA TTTTATTTAG TAATTGATTA TATATGTAG GA       2464
                                                                    Gly

GGA TGG CCT TCC GCA CCT GAT GGA CCA TTC GCA TGG GGT TAC TGT TTC           2512
Gly Trp Pro Ser Ala Pro Asp Gly Pro Phe Ala Trp Gly Tyr Cys Phe
75                  80                      85

CTT AGA GAA CGA GGT AAC CCC GGT GAC TAC TGT TCA CCA AGT AGT CAA           2560
Leu Arg Glu Arg Gly Asn Pro Gly Asp Tyr Cys Ser Pro Ser Ser Gln
90                  95                  100                 105

TGG CCT TGT GCA CCT GGA AGG AAA TAT TTC GGA CGA GGC CCA ATC CAA           2608
Trp Pro Cys Ala Pro Gly Arg Lys Tyr Phe Gly Arg Gly Pro Ile Gln
            110                 115                 120

ATT TCA CA  GTAAGCTACA TAAATCTATA TATGGTAAAA TTTGATGAAC                   2656
Ile Ser His

TTGTAGTGTC TAATTACGTG TATTTGACA TTTCAAAACA G C AAC TAC AAC TAT            2710
                                             Asn Tyr Asn Tyr
                                             125

GGG CCA TGT GGA AGA GCC ATC GGA GTG GAC CTT TTA AAC AAT CCT GAT           2758
Gly Pro Cys Gly Arg Ala Ile Gly Val Asp Leu Leu Asn Asn Pro Asp
130                 135                     140

TTA GTA GCC ACA GAC CCA GTC ATC TCA TTC AAG ACT GCT ATC TGG TTC           2806
Leu Val Ala Thr Asp Pro Val Ile Ser Phe Lys Thr Ala Ile Trp Phe
145                 150                 155                 160

TGG ATG ACC CCT CAA TCA CCA AAG CCT TCT TGC CAC GAT GTC ATC ATT           2854
Trp Met Thr Pro Gln Ser Pro Lys Pro Ser Cys His Asp Val Ile Ile
```

|  |  |  |  | 165 |  |  |  |  | 170 |  |  |  |  | 175 |  |  |
|---|---|---|---|---|---|---|---|---|---|---|---|---|---|---|---|---|
| GGA | AGA | TGG | AAC | CCA | TCT | GCC | GGT | GAC | CGA | TCA | GCC | AAT | CGT | CTT | CCT | 2902 |
| Gly | Arg | Trp | Asn 180 | Pro | Ser | Ala | Gly | Asp 185 | Arg | Ser | Ala | Asn | Arg 190 | Leu | Pro | |
| GGA | TTT | GGT | GTC | ATC | ACA | AAC | ATC | ATC | AAT | GGG | GGC | CTA | GAA | TGT | GGT | 2950 |
| Gly | Phe | Gly 195 | Val | Ile | Thr | Asn | Ile 200 | Ile | Asn | Gly | Gly | Leu 205 | Glu | Cys | Gly | |
| CGT | GGT | AAT | GAC | AAC | AGG | GTA | CAA | GAT | CGA | ATT | GGA | TTT | TAC | AGG | AGG | 2998 |
| Arg | Gly 210 | Asn | Asp | Asn | Arg | Val 215 | Gln | Asp | Arg | Ile | Gly 220 | Phe | Tyr | Arg | Arg | |
| TAT | TGC | GGA | AGCTT |  |  |  |  |  |  |  |  |  |  |  |  | 3012 |
| Tyr 225 | Cys | Gly | | | | | | | | | | | | | | |

( 2 ) INFORMATION FOR SEQ ID NO:6:

( i ) SEQUENCE CHARACTERISTICS:
( A ) LENGTH: 302 amino acids
( B ) TYPE: amino acid
( D ) TOPOLOGY: linear ( i i ) MOLECULE TYPE: protein ( x i ) SEQUENCE DESCRIPTION: SEQ ID NO:6:

| Met -75 | Arg | Arg | Thr | Ser | Lys -70 | Leu | Thr | Thr | Phe | Ser -65 | Leu | Leu | Phe | Ser | Leu -60 |
|---|---|---|---|---|---|---|---|---|---|---|---|---|---|---|---|
| Val | Leu | Leu | Ser | Ala -55 | Ala | Leu | Ala | Gln | Asn -50 | Cys | Gly | Ser | Gln | Gly -45 | Gly |
| Gly | Lys | Val | Cys -40 | Ala | Ser | Gly | Gln | Cys -35 | Cys | Ser | Lys | Phe | Gly -30 | Trp | Cys |
| Gly | Asn | Thr -25 | Asn | Asp | His | Cys | Gly -20 | Ser | Gly | Asn | Cys | Gln -15 | Ser | Gln | Cys |
| Pro | Gly -10 | Gly | Gly | Pro | Gly -5 | Pro | Gly | Pro | Val | Thr | Gly 1 | Gly | Asp | Leu | Gly 5 |
| Ser | Val | Ile | Ser | Asn 10 | Ser | Met | Phe | Asp | Gln 15 | Met | Leu | Lys | His | Arg | Asn 20 |
| Glu | Asn | Ser | Cys 25 | Gln | Gly | Lys | Asn | Asn 30 | Phe | Tyr | Ser | Tyr | Asn 35 | Ala | Phe |
| Ile | Thr | Ala 40 | Ala | Arg | Ser | Phe | Pro 45 | Gly | Phe | Gly | Thr | Ser 50 | Gly | Asp | Ile |
| Asn | Ala 55 | Arg | Lys | Arg | Glu | Ile 60 | Ala | Ala | Phe | Phe | Ala 65 | Gln | Thr | Ser | His |
| Glu 70 | Thr | Thr | Gly | Gly | Trp 75 | Pro | Ser | Ala | Pro | Asp 80 | Gly | Pro | Phe | Ala | Trp 85 |
| Gly | Tyr | Cys | Phe | Leu 90 | Arg | Glu | Arg | Gly | Asn 95 | Pro | Gly | Asp | Tyr | Cys 100 | Ser |
| Pro | Ser | Ser | Gln 105 | Trp | Pro | Cys | Ala | Pro 110 | Gly | Arg | Lys | Tyr | Phe 115 | Gly | Arg |
| Gly | Pro | Ile 120 | Gln | Ile | Ser | His | Asn 125 | Tyr | Asn | Tyr | Gly | Pro 130 | Cys | Gly | Arg |
| Ala | Ile 135 | Gly | Val | Asp | Leu | Leu 140 | Asn | Asn | Pro | Asp | Leu 145 | Val | Ala | Thr | Asp |
| Pro 150 | Val | Ile | Ser | Phe | Lys 155 | Thr | Ala | Ile | Trp | Phe 160 | Trp | Met | Thr | Pro | Gln 165 |
| Ser | Pro | Lys | Pro | Ser 170 | Cys | His | Asp | Val | Ile 175 | Ile | Gly | Arg | Trp | Asn 180 | Pro |
| Ser | Ala | Gly | Asp | Arg 185 | Ser | Ala | Asn | Arg | Leu 190 | Pro | Gly | Phe | Gly | Val 195 | Ile |

-continued

```
Thr  Asn  Ile  Ile  Asn  Gly  Gly  Leu  Glu  Cys  Gly  Arg  Gly  Asn  Asp  Asn
          200                      205                      210

Arg  Val  Gln  Asp  Arg  Ile  Gly  Phe  Tyr  Arg  Arg  Tyr  Cys  Gly
          215                      220                      225
```

(2) INFORMATION FOR SEQ ID NO:7:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO:7:

```
GGATCCATGA  GGCGAACTTC  TAAATTGACT  ACTTTTTCTT  TGCTGTTTTC  TCTGGTTTTG       60

CTGAGTGCTG  C                                                                71
```

(2) INFORMATION FOR SEQ ID NO:8:

(i) SEQUENCE CHARACTERISTICS:
        (A) LENGTH: 163 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO:8:

```
GGCCTGGAAT  GTGGTCGTGG  CAATGACAAT  AGGGTCCAGG  ATCGCATTGG  GTTTTACAGG       60

AGGTATTGCG  GTATTCTTGG  TGTTAGTCCT  GGTGACAATC  TTGATTGCGG  AAACCAGAGA      120

TCTTTTGGAA  ACGGACTTTT  AGTCGATACT  ATGTAATGAG  CTC                         163
```

(2) INFORMATION FOR SEQ ID NO:9:

(i) SEQUENCE CHARACTERISTICS:
        (A) LENGTH: 1863 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO:9:

```
AAGCTTGCAC  GACACACTTG  TCTACTCCAA  AAATATCAAA  GATACAGTCC  TCAGAAGACC       60

AAAGGGCCAA  TTGAGACTTT  TCAACAAAGG  GTAATATCCG  GAAACCTCCT  CGGATTCCAT      120

TGCCCAGCTA  TCTGTCACTT  TATTGTGAAG  ATAGTGGAAA  AGGAAGGTGG  CTCCTACAAA      180

TGCCATCATT  GCGATAAAGG  AAAGGCCATC  GTTGAAGATG  CCTCTGCCGA  CAGTGGTCCC      240

AAAGATGGAC  CCCCACCCAC  GAGGAGCATC  GTGGAAAAAG  AAGACGTTCC  AACCACGTCT      300

TCAAAGCAAG  TGGATTGATG  TGATATCTCC  ACTGACGTAA  GGGATGACGC  ACAATCCAC       360

TATCCTTCGC  AAGACCCTTC  CTCTATATAA  GGAAGTTCAT  TTCATTTGGA  GAGAACACGG      420

GGGACTCTAG  AGGATCCATG  AGGCGAACTT  CTAAATTGAC  TACTTTTTCT  TTGCTGTTTT      480

CTCTGGTTTT  GCTGAGTGCT  GCCTTGGCAC  AGAATTGTGG  TTCACAGGGC  GGAGGCAAAG      540
```

-continued

```
TTTGTGCGTC GGGACAATGT TGCAGCAAAT TCGGGTGGTG CGGTAACACT AATGACCATT      600
GTGGTTCTGG CAATTGTCAA AGTCAGTGTC CAGGTGGCGG CCCTGGTCCT GGTCCTGTTA      660
CTGGTGGGGA CCTCGGAAGC GTCATCTCAA ATTCTATGTT TGATCAAATG CTTAAGCATC      720
GTAACGAAAA TTCTTGTCAA GGAAAGAATA ATTTCTACAG TTACAATGCC TTTATTACTG      780
CTGCTAGGTC TTTTCCTGGC TTTGGTACAA GTGGTGATAT CAATGCCCGT AAAAGGGAAA      840
TTGCTGCTTT CTTTGCCCAA ACCTCCCATG AAACTACTGG TATGTGTATA ACCATTCACA      900
TCGAACCATT AAAATATAAT TTCATTTTAT TTATTTAGT  AATTGATTAT ATATGTAGGA      960
GGATGGCCTT CCGCACCTGA TGGACCATTC GCATGGGGTT ACTGTTTCCT TAGAGAACGA     1020
GGTAACCCCG GTGACTACTG TTCACCAAGT AGTCAATGGC CTTGTGCACC TGGAAGGAAA     1080
TATTTCGGAC GAGGCCCAAT CCAAATTTCA CAGTAAGCTA CATAAATCTA TATATGGTAA     1140
AATTTGATGA ACTTGTAGTG TCTAATTACG TGTATTTTGA CATTTCAAAA CAGCAACTAC     1200
AACTATGGGC CATGTGGAAG AGCCATCGGA GTGGACCTTT TAAACAATCC TGATTTAGTA     1260
GCCACAGACC CAGTCATCTC ATTCAAGACT GCTATCTGGT TCTGGATGAC CCCTCAATCA     1320
CCAAAGCCTT CTTGCCACGA TGTCATCATT GGAAGATGGA ACCCATCTGC CGGTGACCGA     1380
TCAGCCAATC GTCTTCCTGG ATTTGGTGTC ATCACAAACA TCATCAATGG GGGCCTGGAA     1440
TGTGGTCGTG GCAATGACAA TAGGGTCCAG GATCGCATTG GGTTTTACAG GAGGTATTGC     1500
GGTATTCTTG GTGTTAGTCC TGGTGACAAT CTTGATTGCG GAAACCAGAG ATCTTTTGGA     1560
AACGGACTTT TAGTCGATAC TATGTAATGA GCTCGAATTT CCCCGATCGT TCAAACATTT     1620
GGCAATAAAG TTTCTTAAGA TTGAATCCTG TTGCCGGTCT TGCGATGATT ATCATATAAT     1680
TTCTGTTGAA TTACGTTAAG CATGTAATAA TTAACATGTA ATGCATGACG TTATTTATGA     1740
GATGGGTTTT TATGATTAGA GTCCCGCAAT TATACATTTA ATACGCGATA GAAAACAAAA     1800
TATAGCGCGC AAACTAGGAT AAATTATCGC GCGCGGTGTC ATCTATGTTA CTAGATCGAA     1860
TTC                                                                   1863
```

( 2 ) INFORMATION FOR SEQ ID NO:10:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( x i ) SEQUENCE DESCRIPTION: SEQ ID NO:10:

```
AGGGCCGCCA CCTGGACACT GA                                               22
```

( 2 ) INFORMATION FOR SEQ ID NO:11:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:11:

```
Gly Gly Xaa Leu Gly Ser Val Ile Ser Asn Xaa Met Phe Xaa Gln Met
 1               5                  10                  15
Leu Lys Xaa Arg
         20
```

(2) INFORMATION FOR SEQ ID NO:12:

(i) SEQUENCE CHARACTERISTICS:
        (A) LENGTH: 1163 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (ix) FEATURE:
        (A) NAME/KEY: intron
        (B) LOCATION: 449..527
        (D) OTHER INFORMATION: /number=1

(ix) FEATURE:
        (A) NAME/KEY: intron
        (B) LOCATION: 682..762
        (D) OTHER INFORMATION: /number=2

(ix) FEATURE:
        (A) NAME/KEY: CDS
        (B) LOCATION: join(7..448, 528..681, 763..1153)

(ix) FEATURE:
        (A) NAME/KEY: sig_peptide
        (B) LOCATION: 7..231

(ix) FEATURE:
        (A) NAME/KEY: mat_peptide
        (B) LOCATION: join(232..448, 528..681, 763..1153)

(xi) SEQUENCE DESCRIPTION: SEQ ID NO:12:

```
GGATCC ATG AGG CGA ACT TCT AAA TTG ACT ACT TTT TCT TTG CTG TTT              48
       Met Arg Arg Thr Ser Lys Leu Thr Thr Phe Ser Leu Leu Phe
       -75             -70                     -65

TCT CTG GTT TTG CTG AGT GCT GCC TTG GCA CAG AAT TGT GGT TCA CAG              96
Ser Leu Val Leu Leu Ser Ala Ala Leu Ala Gln Asn Cys Gly Ser Gln
    -60             -55                     -50

GGC GGA GGC AAA GTT TGT GCG TCG GGA CAA TGT TGC AGC AAA TTC GGG             144
Gly Gly Gly Lys Val Cys Ala Ser Gly Gln Cys Cys Ser Lys Phe Gly
-45             -40                     -35                 -30

TGG TGC GGT AAC ACT AAT GAC CAT TGT GGT TCT GGC AAT TGT CAA AGT             192
Trp Cys Gly Asn Thr Asn Asp His Cys Gly Ser Gly Asn Cys Gln Ser
                -25             -20                     -15

CAG TGT CCA GGT GGC GGC CCT GGT CCT GGT CCT GTT ACT GGT GGG GAC             240
Gln Cys Pro Gly Gly Gly Pro Gly Pro Gly Pro Val Thr Gly Gly Asp
            -10             -5                          1

CTC GGA AGC GTC ATC TCA AAT TCT ATG TTT GAT CAA ATG CTT AAG CAT             288
Leu Gly Ser Val Ile Ser Asn Ser Met Phe Asp Gln Met Leu Lys His
        5                   10                  15

CGT AAC GAA AAT TCT TGT CAA GGA AAG AAT AAT TTC TAC AGT TAC AAT             336
Arg Asn Glu Asn Ser Cys Gln Gly Lys Asn Asn Phe Tyr Ser Tyr Asn
20              25                  30                      35

GCC TTT ATT ACT GCT GCT AGG TCT TTT CCT GGC TTT GGT ACA AGT GGT             384
Ala Phe Ile Thr Ala Ala Arg Ser Phe Pro Gly Phe Gly Thr Ser Gly
            40                  45                  50

GAT ATC AAT GCC CGT AAA AGG GAA ATT GCT GCT TTC TTT GCC CAA ACC             432
Asp Ile Asn Ala Arg Lys Arg Glu Ile Ala Ala Phe Phe Ala Gln Thr
                55              60                  65

TCC CAT GAA ACT ACT  G GTATGTGTAT AACCATTCAC ATCGAACCAT                     478
Ser His Glu Thr Thr
        70

TAAAATATAA TTTCATTTTA TTTTATTTAG TAATTGATTA TATATGTAG  GA GGA               532
                                                        Gly Gly
```

| | | | | | | | | | | | | | | | | |
|---|---|---|---|---|---|---|---|---|---|---|---|---|---|---|---|---|
|TGG|CCT|TCC|GCA|CCT|GAT|GGA|CCA|TTC|GCA|TGG|GGT|TAC|TGT|TTC|CTT|580|
|Trp|Pro|Ser|Ala|Pro|Asp|Gly|Pro|Phe|Ala|Trp|Gly|Tyr|Cys|Phe|Leu||
|75| | | |80| | | |85| | | | | | |90| |

| | | | | | | | | | | | | | | | | |
|---|---|---|---|---|---|---|---|---|---|---|---|---|---|---|---|---|
|AGA|GAA|CGA|GGT|AAC|CCC|GGT|GAC|TAC|TGT|TCA|CCA|AGT|AGT|CAA|TGG|628|
|Arg|Glu|Arg|Gly|Asn|Pro|Gly|Asp|Tyr|Cys|Ser|Pro|Ser|Ser|Gln|Trp| |
| | | | |95| | | |100| | | | |105| | | |

| | | | | | | | | | | | | | | | | |
|---|---|---|---|---|---|---|---|---|---|---|---|---|---|---|---|---|
|CCT|TGT|GCA|CCT|GGA|AGG|AAA|TAT|TTC|GGA|CGA|GGC|CCA|ATC|CAA|ATT|676|
|Pro|Cys|Ala|Pro|Gly|Arg|Lys|Tyr|Phe|Gly|Arg|Gly|Pro|Ile|Gln|Ile| |
| | | |110| | | | |115| | | |120| | | | |

| | | | | | | | |
|---|---|---|---|---|---|---|---|---|
|TCA|CA|GTAAGCTACA|TAAATCTATA|TATGGTAAAA|TTTGATGAAC|TTGTAGTGTC| |731|
|Ser|His| | | | | | | |

| | | | | | | | |
|---|---|---|---|---|---|---|---|---|
|TAATTACGTG|TATTTTGACA|TTTCAAAACA|G|C|AAC|TAC|AAC TAT GGG CCA TGT|784|
| | | | | |Asn|Tyr|Asn Tyr Gly Pro Cys| |
| | | | | |125| |130| |

| | | | | | | | | | | | | | | | | |
|---|---|---|---|---|---|---|---|---|---|---|---|---|---|---|---|---|
|GGA|AGA|GCC|ATC|GGA|GTG|GAC|CTT|TTA|AAC|AAT|CCT|GAT|TTA|GTA|GCC|832|
|Gly|Arg|Ala|Ile|Gly|Val|Asp|Leu|Leu|Asn|Asn|Pro|Asp|Leu|Val|Ala| |
| | | |135| | | | |140| | | |145| | | | |

| | | | | | | | | | | | | | | | | |
|---|---|---|---|---|---|---|---|---|---|---|---|---|---|---|---|---|
|ACA|GAC|CCA|GTC|ATC|TCA|TTC|AAG|ACT|GCT|ATC|TGG|TTC|TGG|ATG|ACC|880|
|Thr|Asp|Pro|Val|Ile|Ser|Phe|Lys|Thr|Ala|Ile|Trp|Phe|Trp|Met|Thr| |
| | |150| | | | |155| | | |160| | | | | |

| | | | | | | | | | | | | | | | | |
|---|---|---|---|---|---|---|---|---|---|---|---|---|---|---|---|---|
|CCT|CAA|TCA|CCA|AAG|CCT|TCT|TGC|CAC|GAT|GTC|ATC|ATT|GGA|AGA|TGG|928|
|Pro|Gln|Ser|Pro|Lys|Pro|Ser|Cys|His|Asp|Val|Ile|Ile|Gly|Arg|Trp| |
| |165| | | | |170| | | | |175| | | | | |

| | | | | | | | | | | | | | | | | |
|---|---|---|---|---|---|---|---|---|---|---|---|---|---|---|---|---|
|AAC|CCA|TCT|GCC|GGT|GAC|CGA|TCA|GCC|AAT|CGT|CTT|CCT|GGA|TTT|GGT|976|
|Asn|Pro|Ser|Ala|Gly|Asp|Arg|Ser|Ala|Asn|Arg|Leu|Pro|Gly|Phe|Gly| |
|180| | | | |185| | | | |190| | | | |195| |

| | | | | | | | | | | | | | | | | |
|---|---|---|---|---|---|---|---|---|---|---|---|---|---|---|---|---|
|GTC|ATC|ACA|AAC|ATC|ATC|AAT|GGG|GGC|CTG|GAA|TGT|GGT|CGT|GGC|AAT|1024|
|Val|Ile|Thr|Asn|Ile|Ile|Asn|Gly|Gly|Leu|Glu|Cys|Gly|Arg|Gly|Asn| |
| | | | |200| | | |205| | | | |210| | | |

| | | | | | | | | | | | | | | | | |
|---|---|---|---|---|---|---|---|---|---|---|---|---|---|---|---|---|
|GAC|AAT|AGG|GTC|CAG|GAT|CGC|ATT|GGG|TTT|TAC|AGG|AGG|TAT|TGC|GGT|1072|
|Asp|Asn|Arg|Val|Gln|Asp|Arg|Ile|Gly|Phe|Tyr|Arg|Arg|Tyr|Cys|Gly| |
| | | |215| | | | |220| | | | |225| | | |

| | | | | | | | | | | | | | | | | |
|---|---|---|---|---|---|---|---|---|---|---|---|---|---|---|---|---|
|ATT|CTT|GGT|GTT|AGT|CCT|GGT|GAC|AAT|CTT|GAT|TGC|GGA|AAC|CAG|AGA|1120|
|Ile|Leu|Gly|Val|Ser|Pro|Gly|Asp|Asn|Leu|Asp|Cys|Gly|Asn|Gln|Arg| |
| | |230| | | | |235| | | | |240| | | | |

| | | | | | | | | | |
|---|---|---|---|---|---|---|---|---|---|
|TCT|TTT|GGA|AAC|GGA|CTT|TTA|GTC|GAT|ACT ATG TAATGAGCTC|1163|
|Ser|Phe|Gly|Asn|Gly|Leu|Leu|Val|Asp|Thr Met| |
| |245| | | | |250| | | | |

(2) INFORMATION FOR SEQ ID NO:13:

(i) SEQUENCE CHARACTERISTICS:
        (A) LENGTH: 329 amino acids
        (B) TYPE: amino acid
        (D) TOPOLOGY: linear (ii) MOLECULE TYPE: protein (xi) SEQUENCE DESCRIPTION: SEQ ID NO:13:

| | | | | | | | | | | | | | | |
|---|---|---|---|---|---|---|---|---|---|---|---|---|---|---|
|Met|Arg|Arg|Thr|Ser|Lys|Leu|Thr|Thr|Phe|Ser|Leu|Leu|Phe|Ser|Leu|
|-75| | | | |-70| | | |-65| | | | |-60|

| | | | | | | | | | | | | | | |
|---|---|---|---|---|---|---|---|---|---|---|---|---|---|---|
|Val|Leu|Leu|Ser|Ala|Ala|Leu|Ala|Gln|Asn|Cys|Gly|Ser|Gln|Gly|Gly|
| | | | |-55| | | |-50| | | | |-45| | |

| | | | | | | | | | | | | | | |
|---|---|---|---|---|---|---|---|---|---|---|---|---|---|---|
|Gly|Lys|Val|Cys|Ala|Ser|Gly|Gln|Cys|Ser|Lys|Phe|Gly|Trp|Cys|
| | | |-40| | | |-35| | | | |-30| | |

| | | | | | | | | | | | | | | |
|---|---|---|---|---|---|---|---|---|---|---|---|---|---|---|
|Gly|Asn|Thr|Asn|Asp|His|Cys|Gly|Ser|Gly|Asn|Cys|Gln|Ser|Gln|Cys|
| | |-25| | | |-20| | | | |-15| | | | |

| | | | | | | | | | | | | | | |
|---|---|---|---|---|---|---|---|---|---|---|---|---|---|---|
|Pro|Gly|Gly|Gly|Pro|Gly|Pro|Gly|Pro|Val|Thr|Gly|Gly|Asp|Leu|Gly|
| |-10| | | | |-5| | | | |1| | | |5|

| | | | | | | | | | | | | | | |
|---|---|---|---|---|---|---|---|---|---|---|---|---|---|---|
|Ser|Val|Ile|Ser|Asn|Ser|Met|Phe|Asp|Gln|Met|Leu|Lys|His|Arg|Asn|

```
                         10                      15                        20
Glu  Asn  Ser  Cys  Gln  Gly  Lys  Asn  Asn  Phe  Tyr  Ser  Tyr  Asn  Ala  Phe
               25                      30                     35

Ile  Thr  Ala  Ala  Arg  Ser  Phe  Pro  Gly  Phe  Gly  Thr  Ser  Gly  Asp  Ile
          40                      45                     50

Asn  Ala  Arg  Lys  Arg  Glu  Ile  Ala  Ala  Phe  Phe  Ala  Gln  Thr  Ser  His
     55                           60                     65

Glu  Thr  Thr  Gly  Gly  Trp  Pro  Ser  Ala  Pro  Asp  Gly  Pro  Phe  Ala  Trp
70                            75                 80                           85

Gly  Tyr  Cys  Phe  Leu  Arg  Glu  Arg  Gly  Asn  Pro  Gly  Asp  Tyr  Cys  Ser
                    90                      95                     100

Pro  Ser  Ser  Gln  Trp  Pro  Cys  Ala  Pro  Gly  Arg  Lys  Tyr  Phe  Gly  Arg
               105                      110                    115

Gly  Pro  Ile  Gln  Ile  Ser  His  Asn  Tyr  Asn  Tyr  Gly  Pro  Cys  Gly  Arg
          120                      125                    130

Ala  Ile  Gly  Val  Asp  Leu  Leu  Asn  Asn  Pro  Asp  Leu  Val  Ala  Thr  Asp
          135                      140                    145

Pro  Val  Ile  Ser  Phe  Lys  Thr  Ala  Ile  Trp  Phe  Trp  Met  Thr  Pro  Gln
150                      155                      160                         165

Ser  Pro  Lys  Pro  Ser  Cys  His  Asp  Val  Ile  Ile  Gly  Arg  Trp  Asn  Pro
                    170                      175                    180

Ser  Ala  Gly  Asp  Arg  Ser  Ala  Asn  Arg  Leu  Pro  Gly  Phe  Gly  Val  Ile
               185                      190                    195

Thr  Asn  Ile  Ile  Asn  Gly  Gly  Leu  Glu  Cys  Gly  Arg  Gly  Asn  Asp  Asn
          200                      205                    210

Arg  Val  Gln  Asp  Arg  Ile  Gly  Phe  Tyr  Arg  Arg  Tyr  Cys  Gly  Ile  Leu
     215                           220                    225

Gly  Val  Ser  Pro  Gly  Asp  Asn  Leu  Asp  Cys  Gly  Asn  Gln  Arg  Ser  Phe
230                           235                 240                         245

Gly  Asn  Gly  Leu  Leu  Val  Asp  Thr  Met
                    250
```

( 2 ) INFORMATION FOR SEQ ID NO:14:

( i ) SEQUENCE CHARACTERISTICS:
        ( A ) LENGTH: 905 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

```
ATGAGGCGAA  CTTCTAAATT  GACTACTTTT  TCTTTGCTGT  TTTCTCTGGT  TTTGCTGAGT    60
GCTGCCTTGG  CACAGAATTG  TGGTTCACAG  GGCGGAGGCA  AAGTTTGTGC  GTCGGGACAA   120
TGTTGCAGCA  AATTCGGGTG  GTGCGGTAAC  ACTAATGACC  ATTGTGGTTC  TGGCAATTGT   180
CAAAGTCAGT  GTCCAGGTGG  CGGCCCTGGT  CCTGGTCCTG  TTACTGGTGG  GGACCTCGGA   240
AGCGTCATCT  CAAATTCTAT  GTTTGATCAA  ATGCTTAAGC  ATCGTAACGA  AAATTCTTGT   300
CAAGGAAAGA  ATAATTTCTA  CAGTTACAAT  GCCTTTATTA  CTGCTGCTAG  GTCTTTTCCT   360
GGCTTTGGTA  CAAGTGGTGA  TATCAATGCC  CGTAAAAGGG  AAATTGCTGC  TTTCTTTGCC   420
CAAACCTCCC  ATGAAACTAC  TGGAGGATGG  CCTTCCGCAC  TGATGGACC   ATTCGCATGG   480
GGTTACTGTT  TCCTTAGAGA  ACGAGGTAAC  CCCGGTGACT  ACTGTTCACC  AAGTAGTCAA   540
TGGCCTTGTG  CACCTGGAAG  GAAATATTTC  GGACGAGGCC  AATCCAAAT   TTCACACAAC   600
```

-continued

| | | | | | | |
|---|---|---|---|---|---|---|
| TACAACTATG | GGCCATGTGG | AAGAGCCATC | GGAGTGGACC | TTTTAAACAA | TCCTGATTTA | 660 |
| GTAGCCACAG | ACCCAGTCAT | CTCATTCAAG | ACTGCTATCT | GGTTCTGGAT | GACCCCTCAA | 720 |
| TCACCAAAGC | CTTCTTGCCA | CGATGTCATC | ATTGGAAGAT | GGAACCCATC | TGCCGGTGAC | 780 |
| CGATCAGCCA | ATCGTCTTCC | TGGATTTGGT | GTCATCACAA | ACATCATCAA | TGGGGGCCTG | 840 |
| GAATGTGGTC | GTGGCAATGA | CAATAGGGTC | CAAGATCGCA | TTGGGTTTTA | CAGGAGGTAT | 900 |
| TGCGG | | | | | | 905 |

( 2 ) INFORMATION FOR SEQ ID NO:15:

( i ) SEQUENCE CHARACTERISTICS:
( A ) LENGTH: 943 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:15:

| | | | | | | |
|---|---|---|---|---|---|---|
| TCTCTCCTAC | TCCTCTCTGC | CTCGGCAGAA | CAATGTGGTT | CGCAGGCGGG | AGGTGCGCGT | 60 |
| TGTGCCTCGG | GTCTCTGCTG | CAGCAAATTT | GGTTGGTGTG | GTAACACCAA | TGACTATTGT | 120 |
| GGCCCTGGCA | ATTGCCAGAG | CCAGTGCCCT | GGTGGTCCCA | CACCACCCGG | TGGTGGGGAT | 180 |
| CTCGGCAGTA | TCATCTCAAG | TTCCATGTTT | GATCAGATGC | TTAAGCATCG | CAACGATAAT | 240 |
| GCATGCCAAG | GAAAGGGATT | CTACAGTTAC | AATGCCTTTA | TCAATGCTGC | TAGGTCTTTT | 300 |
| CCTGGCTTTG | GTACTAGTGG | TGATACCACT | GCCCGTAAAA | GAGAAATCGC | GGCTTTCTTC | 360 |
| GCCCAAACCT | CCCATGAAAC | TACAGGAGGA | TGGGCAACAG | CACCAGATGG | TCCATACGCG | 420 |
| TGGGGTTACT | GCTGGCTTAG | AGAACAAGGT | AGCCCCGGCG | ACTACTGTAC | ACCAAGTGGT | 480 |
| CAGTGGCCTT | GTGCTCCTGG | TCGGAAATAT | TTCGGACGAG | GCCCCATCCA | AATTTCACAC | 540 |
| AACTACAACT | ACGGACCTTG | TGGAAGAGCC | ATAGGAGTGG | ACCTCCTAAA | CAATCCTGAT | 600 |
| TTAGTGGCCA | CAGATCCAGT | AATCTCATTC | AAGTCAGCTC | TCTGGTTTTG | GATGACTCCT | 660 |
| CAATCACCAA | AACCTTCTTG | CCACGATGTC | ATCATTGGAA | GATGGCAACC | ATCGTCTGCT | 720 |
| GACCGCGCAG | CCAATCGTCT | CCCTGGATTT | GGTGTCATCA | CGAACATCAT | CAATGGTGGC | 780 |
| TTGGAATGTG | GTCGTGGCAC | TGACTCAAGG | GTCCAGGATC | GCATTGGGTT | TTACAGGAGG | 840 |
| TATTGCAGTA | TTCTTGGTGT | TAGTCCTGGT | GACAATCTTG | ATTGCGGAAA | CCAGAGGTCT | 900 |
| TTTGGAAACG | GACTTTAGT | CGATACTATG | TAATTTTATG | GTC | | 943 |

We claim:

1. An isolated, purified gene that comprises a first polynucleotide encoding a polypeptide that has endochitinase activity and that has the sequence (SEQ ID NO: 1).

2. An isolated, purified gene according to claim 1 wherein said gene further comprises a second polynucleotide encoding the polypeptide of the sequence (SEQ ID NO: 2) immediately upstream of said first polynucleotide.

3. An isolated, purified gene according to claim 1, wherein said gene further comprises a polynucleotide encoding a signal peptide upstream of the sequence (SEQ ID NO: 1).

4. An isolated, purified gene according to claim 2, wherein said gene further comprises a third polynucleotide encoding the polypeptide of the sequence (SEQ ID NO: 3) immediately upstream of said second polynucleotide.

5. An isolated, purified gene according to claim 1, wherein the region of said gene encoding said polypeptide comprises genomic or complementary DNA from the 5' portion of the coding sequence of a tomato endochitinase gene and genomic or complementary DNA from the 3' portion of the coding sequence of a tobacco endochitinase gene.

6. An isolated, purified gene according to claim 5, wherein said region comprises at least one intron.

7. An isolated, purified gene according to claim 5, wherein said region comprises the sequence (SEQ ID NO: 4).

8. An isolated, purified gene according to claim 7, further comprising a sequence containing the 35S promoter of cauliflower mosaic virus.

9. An isolated, purified gene according to claim 7, further comprising a sequence containing the nopaline synthase terminator of *Agrobacterium tumefaciens*.

10. A plant cell which is transformed by an isolated, purified gene that comprises a first polynucleotide encoding a polypeptide that has endochitinase activity and that has the sequence (SEQ ID NO: 1).

11. A plant cell according to claim 10, which belongs to one of the species *Nicotiana tabacum, Helianthus annuus* or *Brassica napus*.

12. A plant or plant part, which contains an isolated, purified gene that comprises a polynucleotide encoding a polypeptide that has endochitinase activity and that has the sequence (SEQ ID NO. 1).

13. A plant or plant part according to claim 12, which belongs to one of the species *Nicotiana tabacum, Helianthus annuus* or *Brassica napus*.

14. A plant part according to claim 12, which plant part is a seed.

15. A method for obtaining tobacco or rape plants resistant to chitin-containing pathogens, which comprises (i) transforming tobacco or rare plant cells with an isolated, purified gene which comprises a first polynucleotide encoding a polypeptide of the sequence (SEQ ID NO: 1), said polypeptide having endochitinase activity, (ii) multiplying said transformed cells, and (iii) regenerating said plants.

16. A method according to claim 15, which is applied to one of the species *Nicotiana tabacum* or *Brassica napus*.

17. A method for obtaining a polypeptide, said method comprising the steps of (i) culturing plant cells or calluses containing, in a context capable of permitting its expression, an isolated, purified gene that comprises a first polynucleotide encoding a polypeptide that has endochitinase activity and that has the sequence (SEQ ID NO: 1), (ii) lysing said cells or calluses, and (iii) isolating and purifying said polypeptide.

18. A method according to claim 17, wherein said plant cells or calluses are selected from one of the species *Nicotiana tabacum, Helianthus annuus* or *Brassica napus*.

* * * * *